(12) United States Patent
Forssmann et al.

(10) Patent No.: US 7,741,292 B2
(45) Date of Patent: Jun. 22, 2010

(54) METHOD OF INHIBITING THE EMIGRATION OF CELLS FROM THE INTRAVASCULAR COMPARTMENT INTO TISSUES

(75) Inventors: Ulf Forssmann, Hannover (DE); Jörn Elsner, Hannover (DE); Sylvia Escher, Hannover (DE); Nikolaj Spodsberg, Copenhaven (DK)

(73) Assignee: IPF Pharmaceuticals GmbH, Hannover (DE)

( * ) Notice: Subject to any disclaimer, the term of this patent is extended or adjusted under 35 U.S.C. 154(b) by 281 days.

(21) Appl. No.: 12/071,392

(22) Filed: Feb. 20, 2008

(65) Prior Publication Data

US 2009/0197814 A1 Aug. 6, 2009

Related U.S. Application Data

(63) Continuation of application No. 10/513,962, filed as application No. PCT/EP03/04872 on May 9, 2003, now abandoned.

(60) Provisional application No. 60/381,802, filed on May 21, 2002.

(30) Foreign Application Priority Data

| May 10, 2002 | (EP) | ................................ 02010573 |
| May 21, 2002 | (EP) | ................................ 02011201 |

(51) Int. Cl.
*A61K 38/08* (2006.01)
(52) U.S. Cl. .................... 514/16; 530/328; 514/825; 514/826; 514/886
(58) Field of Classification Search .................... None
See application file for complete search history.

(56) References Cited

U.S. PATENT DOCUMENTS 6,140,064 A 10/2000 Loetscher et al. ............. 435/7.2

FOREIGN PATENT DOCUMENTS

| BE | EP 1 167 527 A1 | 1/2002 |
| EP | 1 167 527 | 1/2002 |
| WO | WO 99/47158 | 9/1999 |

OTHER PUBLICATIONS

Detheux, 2000, J. Exp. Med., 192, 1501-1508.*
Schulz-Knappe, 1996, J. Exp. Med., 183, 295-299.*
Mosier, 1999, Journal of Virology, 73, 3544-3550.*
Detheux, M., et al., "Natural proteolytic processing of hemofiltrate CC chemokine 1 generates a potent CC chemokine receptor (CCR)1 and CCR5 agonist with anti-HIV properties," The Journal of Experimental Medicine, vol. 192, No. 10, Nov. 20, 2000, pp. 1501-1508, [XP002241991].
Muench, J., et al., "Hemofiltrate CC chemokine 1(9-74) causes effective internalization of CCR5 and is a potent inhibitor of R5-tropic human immunodeficiency virus type 1 strains in primary T cells and macrophages," Antimicrobial Agents and Chemotherapy, vol. 46, No. 4, Apr. 2002, pp. 982-990, [XP002241992].
Teran, L. M., "CCL Chemokines and asthma," Immunology Today, vol. 21, No. 5, May 2000, pp. 235-242, [XP004198513].
Mosier et al., "High Potent RANTES Analogues either Prevent CCR5-Using Human Immunodeficiency Virus Type 1 Infection In Vivo or Rapidly Select for CXCR4-Using Variants" *Journal of Virology*, 73(5):3544-3550 (May 1999).

* cited by examiner

*Primary Examiner*—Andrew D Kosar
*Assistant Examiner*—Satyanarayana R Gudibande
(74) *Attorney, Agent, or Firm*—Jacobson Holman PLLC

(57) ABSTRACT

A method of inhibiting the emigration of cells from the intravascular compartment into tissues (or through any membrane limiting any body compartment from another) by confronting the cells with an agonist specific for receptors involved with migration of said cells via a receptor thereby making the cell unresponsive to further activation.

7 Claims, 15 Drawing Sheets

FIG. 1

| | |
|---|---|
| CCL14[1-74] | TKTESSSRGPYHPSECC (positions 1, 5, 10, 15) |
| CCL14[6-74] | SSRGPYHPSECC |
| CCL14[7-74] | SRGPYHPSECC |
| CCL14[8-74] | RGPYHPSECC |
| CCL14[9-74] | [GP]YHPSECC |
| CCL11 (eotaxin) | [GP]ASVPTCC |
| CCL14[10-74] | PYHPSECC |
| CCL14[11-74] | YHPSECC |
| CCL14[12-74] | HPSECC |
| CRIC-3 | CH₃(CH₂)₇CO-PYHPSECC |
| Bis-NNY-CCL14 | CH₃(CH₂)₇CO-Orn[CH₃(CH₂)₇CO]-PYHPSECC |

METHOD OF INHIBITING THE EMIGRATION OF CELLS FROM THE INTRAVASCULAR COMPARTMENT INTO TISSUES

This is a continuation of Ser. No. 10/513,962, filed, Feb. 8, 2005 now abandoned, which is a 371 of PCT/EP03/004872, filed May 9, 2003, which claims the benefit of U.S. Provisional Application No. 60/381,802, filed May 21, 2002.

BACKGROUND OF THE INVENTION

The role of inflammation in allergic diseases, especially in asthma is widely recognized, and inflammation of the airways is one of the three major characteristics of asthma[1;2]. The major infiltrating effector cells in asthma contributing to the inflammatory response are eosinophils, mast cells and Th2 lymphocytes[3-5] all contributing to a complex pathologic process that ultimately leads to reduced lung function.

The molecular mechanisms involved in the recruitment of these cells from the circulation are complex[6]. Chemokines are of fundamental importance in this multistep process. Being present on the endothelium bound to glycosminoglycans, chemokines trigger integrin activation on rolling leukocytes resulting in their firm adhesion on the endothelial surface[7]. Transendothelial migration of the leukocytes into the surrounding tissue also strongly depends on chemokines and their receptors[8]. Key molecules involved in asthma belonging to the chemokine system have been recently elucidated. CCL11 (eotaxin) was the first specific chemokine identified as an attractant for eosinophils in the bronchoalveolar lavage fluid (BALF) obtained from an experimental model of allergen exposure of sensitized guinea pigs[9] and was subsequently shown to be present in humans[10]. The functionally related chemokines CCL24 (eotaxin-2) and CCL26 (eotaxin-3) were described thereafter[11;12] Besides the eotaxins, the MCPs, CCL5 (RANTES) and a truncated chemokine derived from CCL14 (HCC-1) are attracting the same type of inflammatory cells being involved in asthma[13;14]. An important role of CCL11 for the attraction of eosinophils into the lung was recently shown by several groups in human asthmatic subjects. The influx of eosinophils correlates strongly with increased peptide and mRNA expression of CCL11[15;16].

The common feature of the eotaxins, the MCPs and CCL5 are their ability to mediate chemotaxis via the chemokine receptor CCR3, which has been shown to be expressed on eosinophils[17], mast cells[18], basophils[19], and Th2-cells[20;21]. The involvement of other chemokines was clearly demonstrated in vivo showing that different chemokines, in the majority activators of CCR3, contribute at different levels to the complex pathophysiology of asthma[22]. Only this year a major breakthrough for the extraordinary role of CCR3 in asthma was achieved. Targeted disruption of CCR3 was successfully performed showing that eosinophils and other inflammatory cells were arrested in the subendothelial space of pulmonary vessels after bronchial allergen challenge in OVA-sensitized mice[23], implicating that the local inflammatory response can be abolished targeting CCR3 already in the circulation. Furthermore airway hyperresponsiveness (AHR) is completely abrogated in CCR3-deficient mice in which the animals are sensitized by the epicutaneous route[24]. Therefore the common receptor CCR3 is exceptionally attractive as a drug target, and its blockade is already propagated as a therapy for asthma[25].

CCL14 was recently isolated from human hemofiltrate based on its high concentrations in human blood plasma[26]. The originally isolated molecular form of CCL14 containing 74 amino acid residues was shown to be a very weak activator of monocytes. Later on, chemically synthesized N-terminal truncated forms of CCL14 were shown to be more potent activators of monocytes acting via CCR1[27]. Further screening of human hemofiltrate fractions for novel natural ligands of chemokine receptors led to the identification of the variant CCL-14[9-74], being a potent agonist for CCR1, CCR3, and CCR5[28].

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

FIG. 1: Alignment of N-terminal sequences of CCL14 derivatives and CCL11.

SUMMARY OF THE INVENTION

Figure 2:
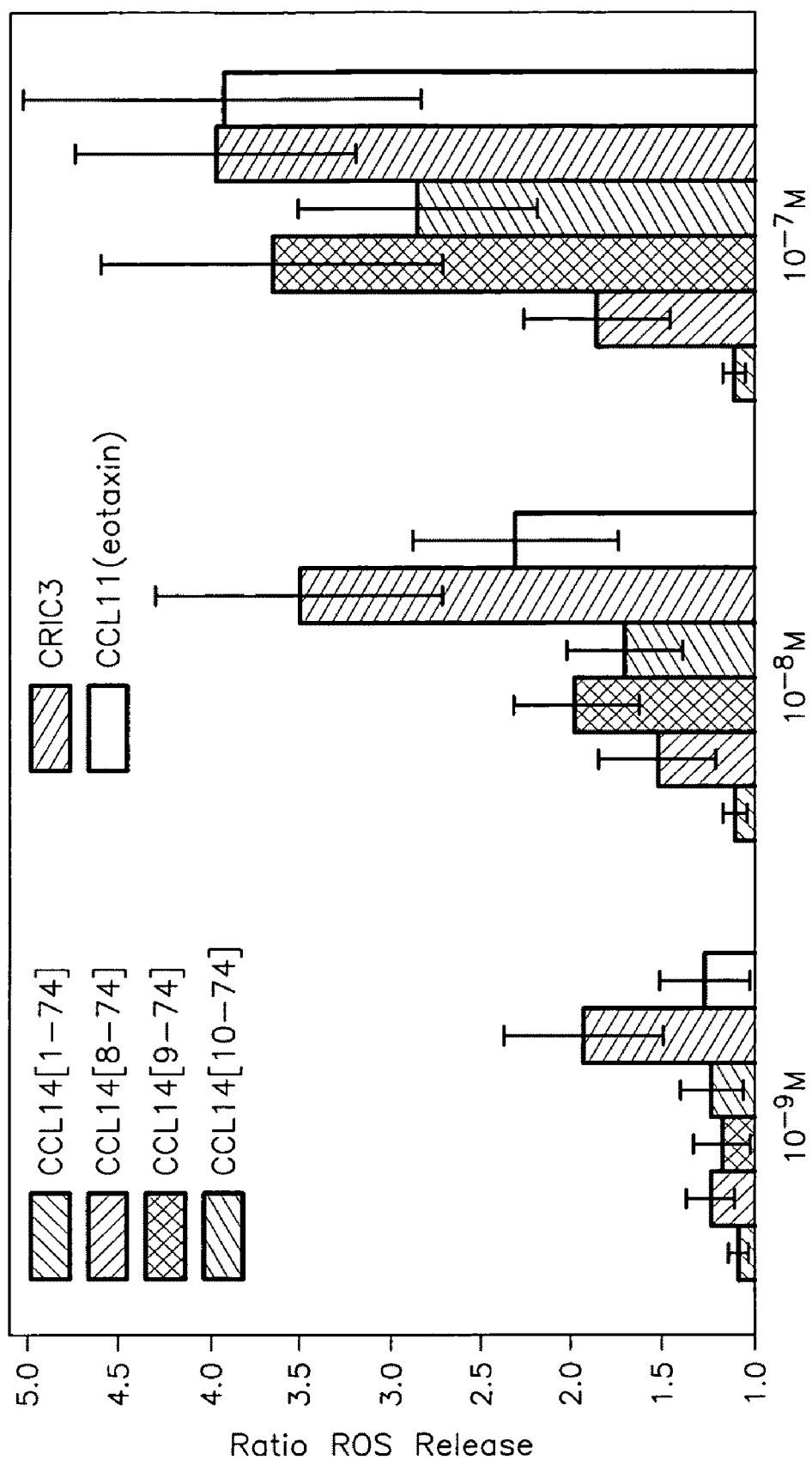
FIG. 2: CRIC3 induces the release of reactive oxygen species (ROS) from human eosinophils with more potency than CCL11.

The chemokine receptor CCR3 is expressed on different inflammatory cells, such as eosinophils, basophils, and $Th_2$ cells, and is responsible for the invasion of these cells to the site of inflammation, particularly in allergic disease. Whereas most anti-inflammatory strategies act on their target cells after migration to the site of inflammation, a method is disclosed on how to prevent the cellular recruitment by inactivation of the chemokine receptor by means of a potent agonist, before blood circulating cells, such as leukocytes, leave the blood vessels. An object of the present invention is therefor to provide a method for preventing the migration of blood circulating cells out of the blood.

Surprisingly, by confronting the cells with an agonist specific for receptors involved with migration of said cells via a receptor, the cell is rendered unresponsive to further activation and is not leaving the blood stream. For this purpose, in particular different truncated and chemically modified peptides derived from the chemokine CCL14 (HCC-1) can be used. Replacement of the ultimate N-terminal amino acid of CCL14[9-74] by nonanoic acid (NNY) converts it into a potent agonist, termed CD26-resistant inactivator of CCR3 (CRIC3) exhibiting an activity profile identical to CCL11 (eotaxin), the most potent chemokine agonist of CCR3 known with respect to the release of reactive oxygen species, chemotaxis, and CCR3-internalization. This modification results in a resistance to degradation by dipeptidyl peptidase IV (CD26/DPP IV) due to the substitution of the Gly-Pro motif by the NNY-Pro motif. In contrast to CRIC3, CCL11 is processed completely by CD26/DPP IV into CCL11[3-74] thereby reducing its biological activity. Interestingly, intravenous administration of CRIC3 in ovalbumin-sensitized mice, prior to allergen challenge, resulted in a significant reduction of eosinophils in the BALF and lung tissue. Therefore, CRIC3 can be used to induce internalization of CCR3 on blood leukocytes in the circulation. As a consequence of the inactivation of CCR3, the recruitment of eosinophils, basophils, and $Th_2$ cells into tissues could be prevented in CCR3-driven pathologies.

The object addressed by the present invention is solved by a method of inhibiting the emigration of blood circulating cells from the blood stream by confronting the cells with an agonist specific for receptors involved with migration of said cells via a receptor thereby making the cell unresponsive to further activation. In particular, the cells are leukocytes.

According to the invention the cell is unresponsive to further activation for emigration to tissues after confrontation with an agonist.

In one embodiment of the invention the agonist used to inhibit the migration of the cells is a chemoattractant binding to a corresponding receptor or molecule binding to such a receptor. The chemoattractant is in particular selected from the group consisting of a chemokine, a defensine, a leukotriene, a formyl-peptide or combinations thereof. The proteins and peptides may exist and can be used also in form of mutants and variants. In particular this may be the case for chemokines. Mutants or variants of peptides differ to some extent in their amino acid sequences from the respective consensus sequence. The alterations may be due to exchanges of single or multiple amino acids or deletions of single or multiple amino acids. For example, so called conservative amino acid exchanges do not significantly change structure and function of the protein or polypeptide. If a hydrophobic amino acid such as Valin is exchanged for example against another hydrophobic amino acid, such as Alanin, this is understood as an example for conservative exchange. Such changes in most instances will not change structure and function of the protein dramatically. Another example for a conservative exchange is for example the exchange of Lysine against another charged amino acid.

A protein is constructed by domains for example a series of hydrophobic or hydrophilic amino acids. If one amino acid is deleted it may also not alter the function and structure dramatically. Mutants and variants can occur naturally, but may also be generated by well known genetic engineering methods such as site directed mutagenesis. The alterations may be such that they do not lead to loss of function of the polypeptide in particular receptor internalisation and desensitisation.

According to the present invention the following compounds can be used:

$R^1$-CCL14[10-74], R1-CXCL12[1-67], R1-CXCL12V3I[1-67], R1-CXCL12[2-67], R1-CXCL12V3I[2-67], R1-CXCL12[1-72], R1-CXCL12V3I[1-72], R1-CXCL12[2-72] and R1-CXCL12V3I[2-72]

wherein $R^1$ is a lypophilic, hydrophobic or polar aprotic residue. A polar aprotic residue is a residue, which shows some polarity, but does not have active hydrogen or can be associate in $H^+$ and an ion. Typical polar aprotics compounds are for example organic ethers. In particular $R^1$ is an organic residue having up to 50 carbon atoms, which may be substituted with heteroatoms and which organic residue is branched, unbranched, saturated, unsaturated or combinations thereof. In a specific embodiment $R^1$ is a residue containing aromatic moieties, polyethylenoxide moieties with 2 to 18 units.

Furthermore, $R^1$ may be any amino acid, or $CH_3—(CH_2)_n—X$; in which $(CH_2)_n$ is branched or unbranched X is —C(O)—NH—$CH_2$—C(O)—, —$NHCH_2$—C(O)—, —ONH—$CH_2$—C(O)—, —$OCH_2$—$CH_2$—C(O)—, —CH═CH—C(O)—, —C(O)—, or a covalent bond; and n is an integer of 1-17;

or pharmaceutically acceptable salt thereof.

It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural processes and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli*, prior to processing, almost invariably will be N-formylmethionine.

It is also an object of the invention to provide a method for the treatment of a patient having need of the agonist comprising administering to the patient a therapeutically effective amount (normally in the range of 1-1,000 nmol/kg body weight) of the ligand, wherein said patient is suffering from a disease or a disorder, including, but not limited to, inflammatory diseases, particularly allergic asthma, atopic dermatitis, and rheumatoid arthritis, infections such as bacterial, fungal, protozoan and viral infections, particularly infections caused by HIV-1 or HIV-2; pain; cancers; diabetes; Parkinson's disease; both acute and congestive heart failure; hypotension; hypertension; urinary retention; osteoporosis; angina pectoris; myocardial infarction; ulcers; allergies; benign prostatic hypertrophy; chronic renal failure; renal disease; impaired glucose tolerance; sexual dysfunction and psychotic and neurological disorders, among others.

The agonists are produced by standardized chemical methods as described later. Alternatively they are produced by recombinant methods, such as phage display or expression cloning in *E. coli*. The agonists are purified and galenically prepared for application using established methods.

The medicaments of the invention are prepared in suitable galenic formulation. Preferred formulations are lyophilized with mannitol or similar carbohydrates in a sterile container. These can be used for repeated injection or continuous infusion upon uptake in a physiologic medium. Preferred amounts are 1 to 1,000 nmol/kg body weight of the patient, calculated on the pure agonist.

Preferably the medicament is a galenic formulation comprising biocompatible microspheres. The route of administration is preferably selected from aerosols, intravenous or subcutaneous application for systemic or local administration.

Subject matter of the present invention is also a method of treating a disease state in mammals that is alleviated by treatment with a compound of the invention, which method comprises administering to an mammal in need of such a treatment a therapeutically effective amount of the compound. In particular the method of the invention is able to inhibit inflammation.

The invention is also concerned with the use of an agonist specific for receptor involved with migration of blood circulating cells from the blood stream for the manufacturing of a medicament for the treatment of diseases associated with migration of blood cells from the blood stream into tissues. According to the invention the agonist is e.g. a chemo-attractant, in particular selected from the group consisting of chemokines, defensines, leukotrienes, formyl-peptides.

The use of a compound selected from the group consisting of $R^1$-CCL14[10-74], R1-CXCL12[1-67], R1-CXCL12V3I [1-67], R1-CXCL12[2-67], R1-CXCL12V3I[2-67], R1-CXCL12[1-72], R1-CXCL12V3I[1-72], R1-CXCL12[2-72] and R1-CXCL12V3I[2-72]

wherein R1 is an aromatic or non-aromatic, branched or unbranched compound comprising 1 to 50 atoms selected from C, H, O, N, S, P, F, Cl, Br and I, preferably $R^1$ is any amino acid, or $CH_3$—$(CH_2)_n$—X; in which $(CH_2)_n$ is branched or unbranched X is —C(O)—NH—$CH_2$—C(O)—, —NHCH$_2$—C(O)—, —ONH—$CH_2$—C(O)—, —O$CH_2$—$CH_2$—C(O)—, —CH=CH—C(O)—, —C(O)—, or a covalent bond; and n is an integer of 1-17;

or pharmaceutically acceptable salt thereof for the manufacturing of a medicament for the treatment of inflammation and tumors, especially their metastatic spread, and to modulate the homing of any cell, such as lymphocytes or stem cells is also subject of the present invention.

The invention discloses and utilizes the effects of the N-terminal modification of CCL14[26;28] on its biological activity mediated via the CCR3. Chemical modification of the most active form was performed with the intention to generate a CCR3-ligand leading to the inactivation of CCR3. Replacement of the ultimate N-terminal amino acid of CCL14[9-74] by nonanoic acid led to the identification of a potent agonistic inactivator of CCR3, being as active as eotaxin, but fully resistant to cleavage by dipeptidyl peptidase IV (CD26/DPP IV, EC 3.4.14.5) and therefore termed CD26-resistant inactivator of CCR3 (CRIC3). CD26/DPP IV is an abundant peptidase found in serum, tissue and on the cell surface of different cell types. It is responsible for the inactivation of chemokines, preferentially due to hydrolysis of peptides with N-terminal Xaa-Pro and Xaa-Ala motifs[29]. Whereas most anti-inflammatory strategies act on the target cells after they migrated to the site of inflammation[30], the present invention discloses a method in which the cellular recruitment is prevented by inactivation of the CCR3 before cells leave the blood vessels. CRIC3 was also able to impair airway influx of CCR3+ eosinophils in OVA-sensitized mice. The application of this compound represents a new concept for the therapy of CCR3-driven pathologies.

The invention is further described by means of the following non-limiting examples.

EXAMPLES

Chemokines

CCL11 and CXCL12 (SDF-1α) were obtained from PeproTech (London, U.K.). C5a was obtained from Sigma (Deisenhofen, Germany). CCL14[1-74] was prepared as previously described[26].

Synthesis of CCL14 Derivatives.

CCL14[6/7/8/9/10/11/12-74] and N-terminally modified derivatives were prepared by Fmoc based solid-phase peptide synthesis as described[31]. The synthesis of CCL14 peptides were carried out on a 433A peptide synthesizer (Applied Biosystems) at a scale of 0.1 mmol with a ten fold excess Fmoc amino acid using HBTU/HOBt activation. After peptide chain assembly, nonanoic acid was coupled as symmetrical anhydride (Sigma-Aldrich, Taufkirchen, Germany) in N-methylpyrrolidinone (65 eq.) to the obtained polypeptide. The resulting peptides were cleaved and deprotected in the presence of TFA:H2O:EDT:phenol (86:6:6:2, v:v:v:w, 15 ml/g), precipitated in cold TBME and purified chromatographically. The resulting chromatographically homogeneous peptides were analyzed by capillary zone electrophoresis and electrospray mass spectrometry. The purified derivatives were used for biological testing according to the net peptide content as determined by amino acid analysis.

Antibodies.

The rat mAb against CCR3 (clone 61828.111; IgG2a) and the murine mAb against CCR1 (IgG2b) were obtained from R&D Systems (Wiesbaden Germany). The rat IgG2a and mouse IgG2b isotype control Ab were obtained from Immunotech (Hamburg, Germany).

Eosinophil Isolation.

Eosinophils were purified from the venous blood of normal nonatopic healthy or atopic donors using Ficoll (Pharmacia, Erlangen, Germany) density gradient centrifugation and a negative selection based on CD16 Microbeads (Miltenyi Biotec, Auburn, Calif.) as described previously[32]. The resulting eosinophil purity was >99% as determined by microscopic examination with Kimura staining.

Lucigenin-Dependent Chemiluminescence.

Lucigenin-dependent chemiluminescence representing a sensitive method to measure the generation of reactive oxygen species (ROS)[33] was performed using a single-photon imaging system with a two-dimensional photon counting system allowing the simultaneous measurement and analysis of 96 wells as previously described in detail[33]. Data are expressed as the ratio between stimulus-induced intensity integral counts and medium-induced intensity integral counts.

Internalization of CCR3.

These experiments were performed as described in detail previously[32;33]. For flow cytometry analysis $10^5$ eosinophils were incubated at 4° C. for 30 min with anti-chemokine receptor mAb or isotype control at the concentrations recommended by the supplier. In a second step the cells were stained by FITC-conjugated goat anti-rat (Immunotech) or goat-anti mouse Ab (Immunotech) and thereafter analyzed by flow cytometry (FACScan, Becton Dickinson, Heidelberg, Germany).

For internalization of CCR3, the cells were preincubated for 30 min at 37° C. with the indicated chemokines in a total volume of 100 µl RPMI 1640 prior to staining. The inhibition of CCR3 internalization was achieved by initial treatment of the cells for 5 min with 8 µM phenylarsine oxide (PAO) at 37° C. and alternatively by treatment of cells with the indicated chemokines at 4° C. Both strategies are suitable to inhibit internalization of 7-transmembraneous receptors from the cell surfaces as described in detail earlier[32].

In Vitro Chemotaxis.

Chemotaxis was assessed in 48-well chambers (Neuro-Probe, Cabin John, Md.) using polyvinylpyrrolidone-free polycarbonate membranes with 5-μm pores (Nucleopore, NeuroProbe, Cabin John, Md.) for $5 \times 10^4$ eosinophils as previously described[11]. For inhibition of CCL11 induced chemotaxis, eosinophils were preincubated for 15 min at room temperature with CRIC3 and thereafter directly placed in the upper compartment of the chemotaxis chamber. Measurement of intracellular calcium concentration $[Ca^{2+}]_i$ Eosinophils were loaded with 2 μM fura-2-AM (Molecular Probes, Eugene, Oreg.) and processed as described previously[13]. Receptor desensitization was tested by monitoring $[Ca^{2+}]_i$ changes in response to sequential stimulation with chemokines as described.

Kinetics of CD26/DPP IV Processing.

To analyze the processing of the naturally occurring chemokine CCL14[9-74] and the modified derivative CRIC3, an in vitro kinetic study was made by incubating 10 μM chemokine with $6.6 \times 10^{-4}$ units of porcine kidney. DPP IV/CD26 [lot: 100K38002, Sigma, Deisenhofen, Germany] in Tris-HCl, pH 7.5 at 37° C. At specific time intervals, the reactions were stopped with 0.1% trifluoroacetic acid and placed on ice. For comparison, the DPP IV/CD26 processing of the previously analyzed chemokines CCL11 and CXCL12[34] were examined in parallel. The composition of the reactions was determined offline with a MALDI mass spectrometer (Voyager DE-Pro, Applied Biosystems, Weiterstadt, Germany) in linear mode accumulating eight spectra of 100 shots each. The instrument uses a high-potential acceleration source (20 kV), and other parameters were optimized for measurement of chemokines.

Animals

Syngenic female Balb/c mice, obtained from Charles River (Sulzfeld, Germany) with an age of 8 weeks and an average weight of 19 g were used in this experiment as described previously[35]. Mice were maintained on laboratory food and tap water ad libitum under pathogen free conditions in a regular 12 h dark/light cycle with a temperature of 22° C. and were allowed to become acclimated to their environment for a period of 7 days prior to experiment.

Protocol of Allergic Sensitization and CRIC3 Treatment

Animals were divided into two groups of n=4. Sensitization of the animals was carried out via the intraperitoneal route on day 0, 14 and 21 each with 10 μg OVA (chicken ovalbumin grade VI, Sigma) together with 1 mg Al(OH)3 (Alum Inject, Pierce, Rockford, Ill.) as adjuvant dissolved in sterile saline[35]. To provoke an allergic airway response, aerosol challenge was performed using a Pari Master nebulisation system (MMAD 2.5 μm) and 1% OVA solution. Animals were exposed to allergen on day 28 for 10 min, yielding to a calculated airway allergen deposition of approximately 10 μg OVA. To examine the inhibitory effect of CRIC3, four mice were treated with 10 nmol/kg CRIC3 diluted in sterile saline (applicated via the tail vein) 30 min prior to allergen exposure and 3 h and 8 h after the challenge. The other group was injected with sterile saline at identical time points.

BALF and Histological Evaluation

Animals were sacrificed 24 h after OVA-challenge by injecting an overdose of pentobarbital-Na (Narcoren®) intraperitoneally[35]. The trachea was cannulated, airways were lavaged with 0.8 ml cold 0.9% NaCl, and lung dissection was performed. Total cell numbers in BALF were counted and cytospins were evaluated. The left lungs were dissected and fixed in formalin for further histological examinations using hematoxylin-eosin staining[35].

Statistical Analysis

The number of experiments is stated in the legends of the FIGS. as n and represents different donors. Unless otherwise stated, the data in the text and FIGS. were expressed as mean± standard error of the mean (SEM) as determined by SigmaStat™ (SPSS Inc.) analysis. Values of p<0.05 were accepted as significant using Student's t test.

Results

Derivatives of CCL14.

To characterize the functional importance of the N-terminal domain of CCL14, the biological activity of ten different CCL14 analogues was investigated. These included: CRIC3 (NNY-CCL14[10-74]), Bis-NNY-CCL14[10-74], full size CCL14[1-74] and seven N-terminally truncated variants that have been described previously[26;28;36]. The N-terminal sequences of these derivatives and of CCL11 are shown in FIG. 1.

Human blood eosinophils as a natural system to study the effects of CCL14 derivatives on CCR3.

To study the effects of the CCL14 derivatives on CCR3, freshly isolated human blood eosinophils were used being a natural cell population expressing high surface levels of CCR3. Eighty donors were screened for CCR1 expression and found only two individuals with significant CCR1 surface expression (data not shown), which were excluded from the following experiments.

CCL14 analogs are potent activators of the respiratory burst mediated by CCR3.

First, the effects of all CCL14 derivatives on the release of reactive oxygen species (ROS) were compared using lucigenin-dependent chemiluminescence, which is established as a sensitive method to study effector functions mediated by chemokine receptors on human eosinophils. Among all derivatives studied only CCL14[8-74], [9-74], [10-74] and CRIC3 induced a significant release of ROS at concentrations up to $10^{-7}$ M (FIG. 2). These derivatives were compared at different doses with CCL11, which has been described as the most potent activator of the respiratory burst in eosinophils 37 and CCL14[1-74] as the naturally abundantly occurring form. As shown in FIG. 2, CCL14[9-74] and CRIC3 are as potent as CCL11 in inducing the release of an identical amount of ROS at a concentration of $10^{-7}$ M, while CCL14[8-74] and [10-74] are less potent, and full-length CCL14[1-74] is virtually inactive. CRIC3 is the most potent stimulus tested being already significantly active at a concentration of $10^{-9}$ M (FIG. 2) and almost reaching its maximal effect at $10^{-8}$ M. The inactive analogs were further analyzed for antagonistic effects. Pretreatment of human eosinophils with CCL14[1-74], [6-74], [7-74], [11-74], [12-74] or Bis-NNY-CCL14[10-74] $10^{-7}$ M did not result in significant inhibition of ROS release following stimulation with CCL11 at identical concentrations (data not shown).

CRIC3 induces internalization of CCR3 as efficient as CCL11.

Figure 3A:
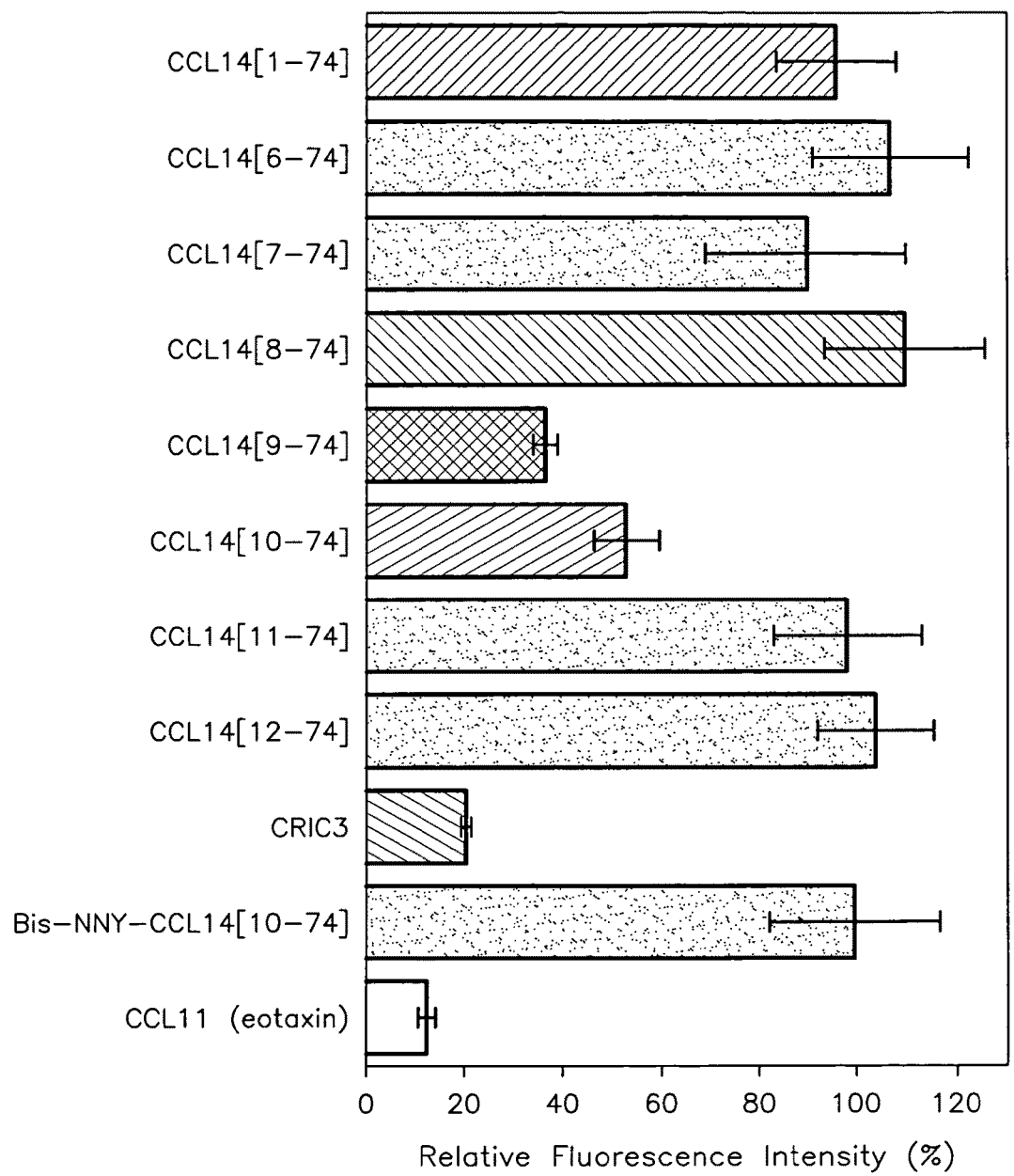
FIG. 3: CRIC3 induces an internalization of CCR3 from human eosinophils in the same range than CCL11.
Figure 3B:
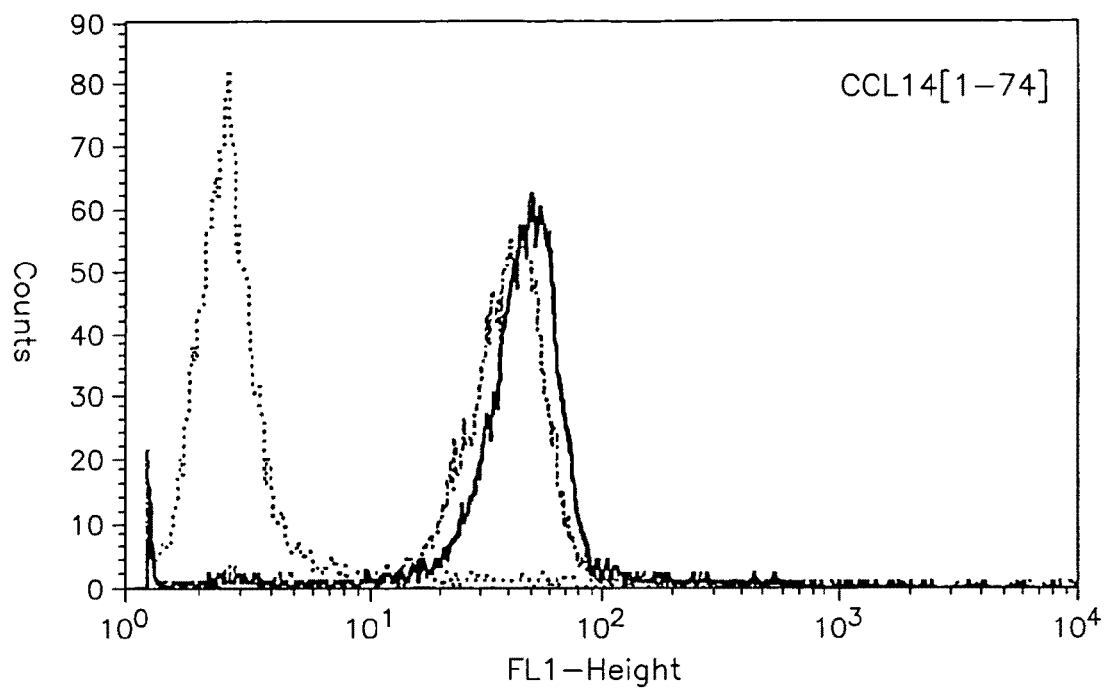
Figure 3B:
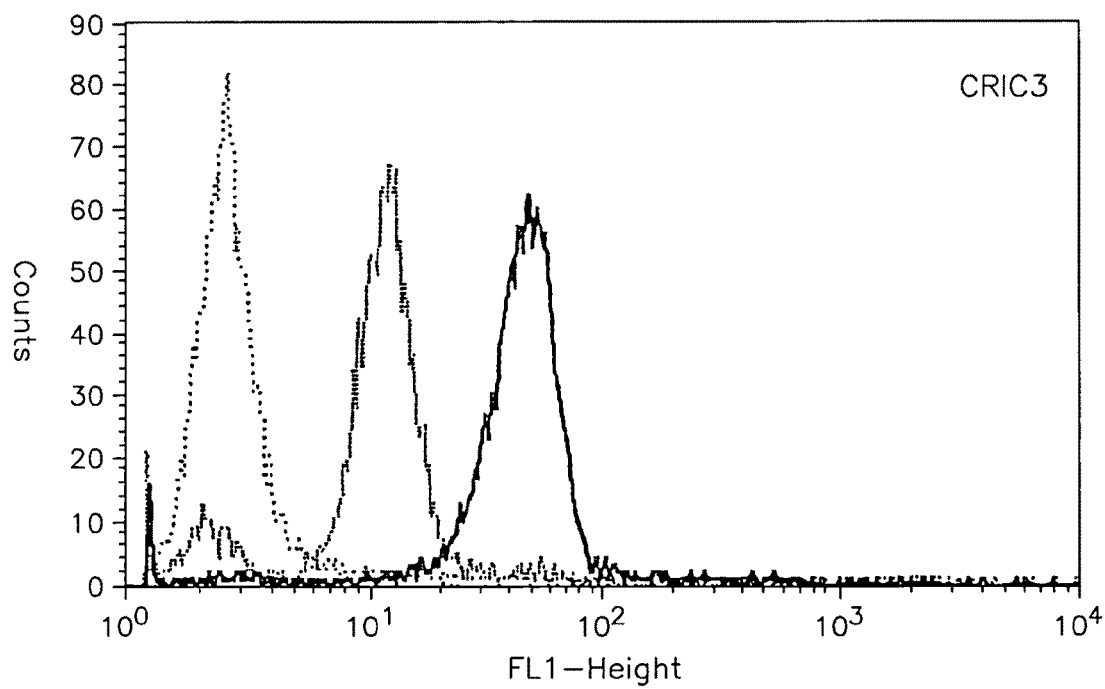
Figure 3B:
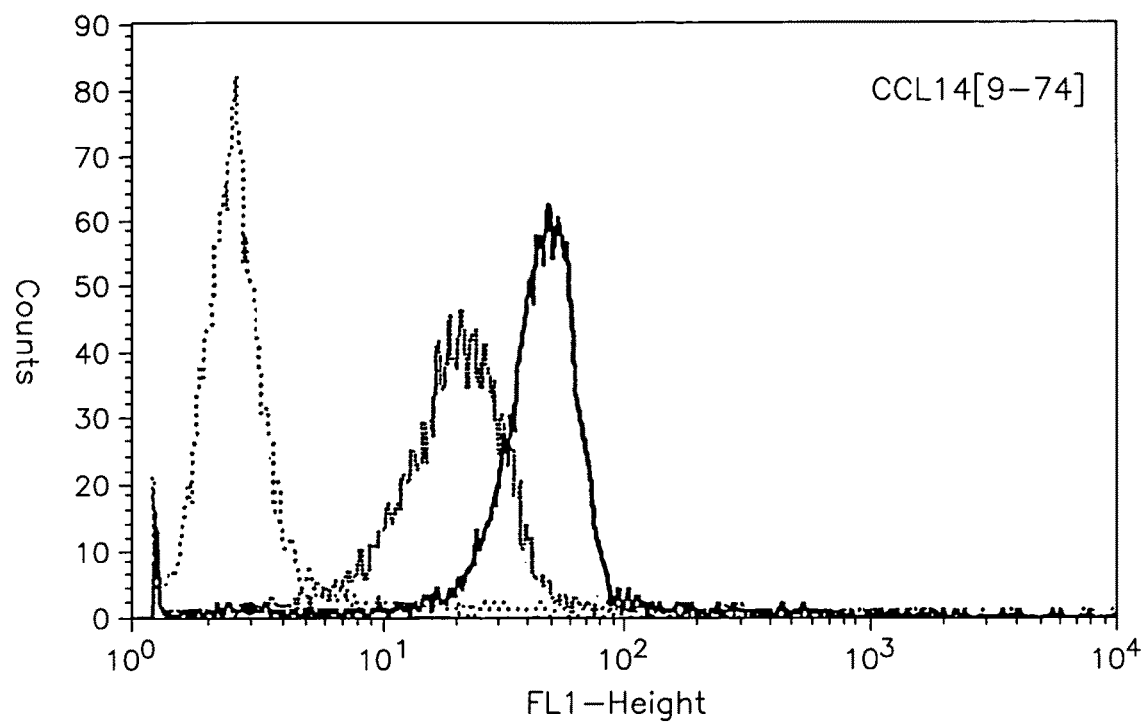
Figure 3B:
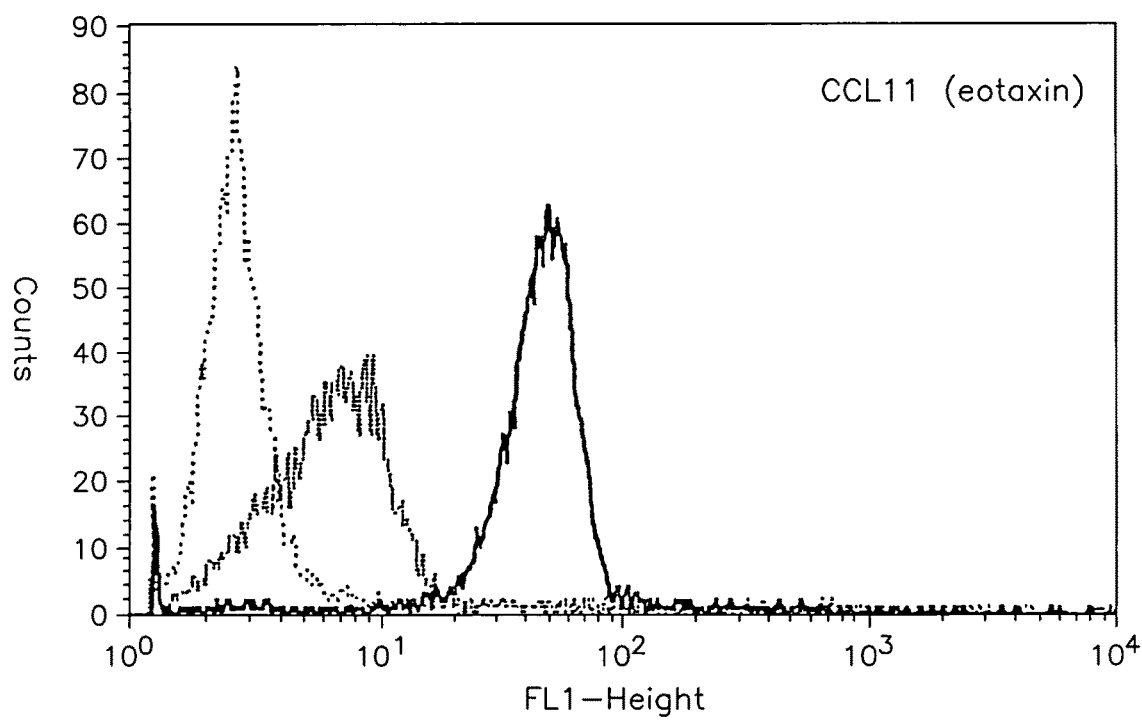

In the next set of experiments, human eosinophils were incubated for 30 min with all CCL14 derivatives or CCL11 as positive control at a concentration of $10^{-7}$ M at 37° C. The cells were then stained with anti-CCR3 mAb and receptor expression was measured by flow cytometry. Preincubation of human eosinophils with CCL14[9-74], CCL14[10-74], and CRIC3 led to a significant down-regulation of CCR3 (FIGS. 3a and b). The other derivatives including CCL14 [8-74], which was a weak inducer of ROS, did not affect CCR3 expression (FIG. 3a). At optimal doses CRIC3 and CCL11 both removed 80% of cell surface CCR3 and were significantly more effective than CCL14[9-74] (50%) and CCL14[10-74] (30%). At lower concentrations, CCL11 was superior to all CCL14 derivatives (FIGS. 3a and b).

Figure 3C:
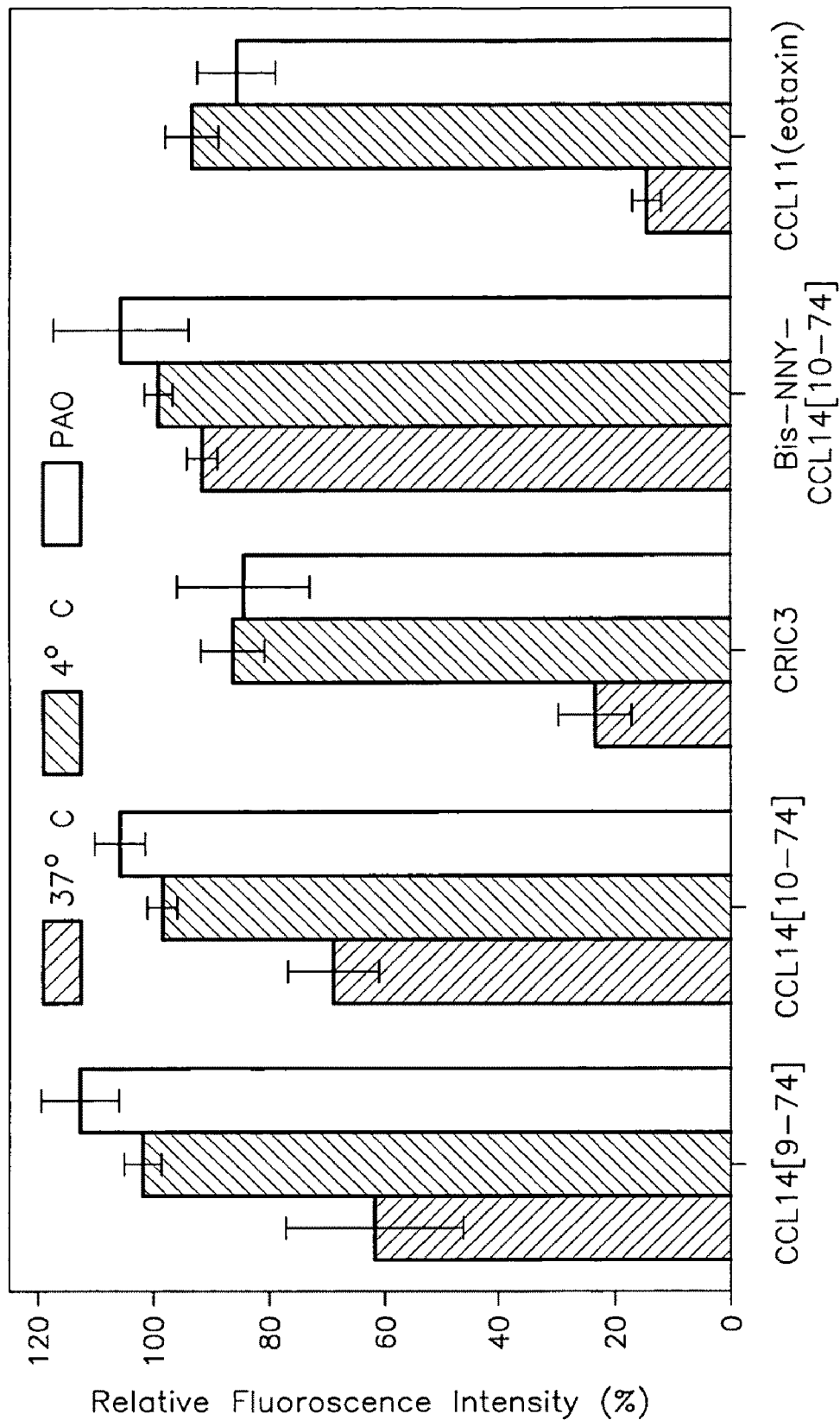

As reduced staining intensity in flow cytometry could also depend on altered receptor accessibility of the antibody after preincubation with ligands, the same experiments were performed with the active ligands at 4° C., a temperature at which receptor internalization is prevented[38]. In the same set of experiments, the influence of PAO on the expression of CCR3 were also studied. PAO inhibits the protein tyrosine phosphatase and has been widely used as a general inhibitor of receptor internalization[32]. Both treatments clearly prevented the disappearance of CCR3, which was between 30% and 80% at 37° C. for the active CCL14 derivatives in the same experimental setting (FIG. 3c). These data clearly show that the induced decrease of cell surface CCR3 on human eosinophils was due to receptor internalization and that CRIC3 induced internalization of CCR3 is as efficient as by CCL11.

CRIC3 is the most potent eosinophil chemoattractant among CCL14 derivatives and inhibits CCL11-induced chemotaxis.

Figure 4A:
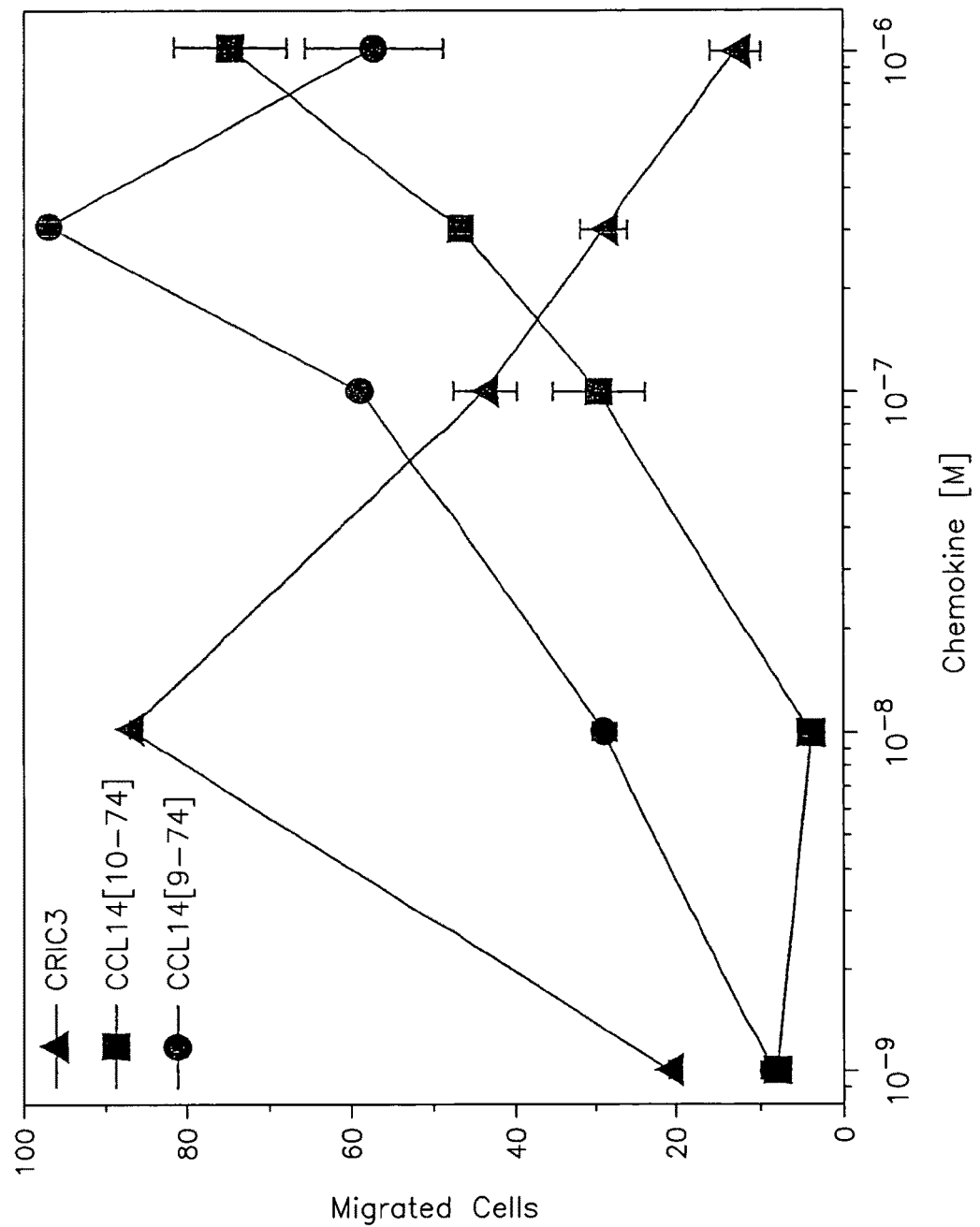
FIG. 4: CRIC3 induces chemotaxis of eosinophils but also inhibits CCL11.
Figure 4B:
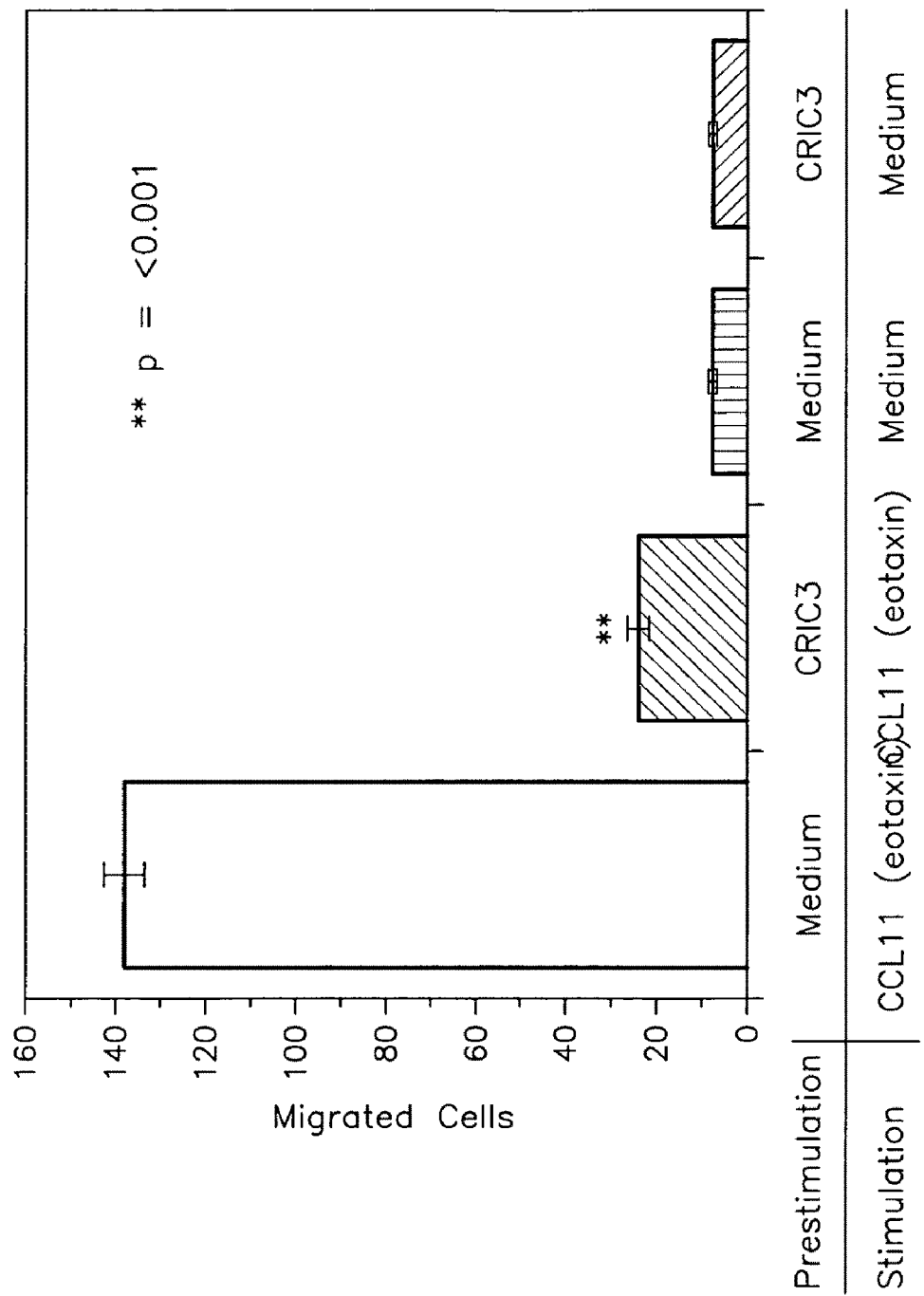

To evaluate whether the most active CCL14 derivatives induce chemotaxis of CCR3-positive cells, migration assays were carried out in 48-well micro chemotaxis chambers. As shown in FIG. 4a CCL14 derivatives are effective chemoattractants for human eosinophils. The activity of the derivatives tested was similar in terms of the efficacy, as indicated by the number of migrated cells. Maximal responses to CCL14[9-74] and CCL14[10-74] were reached at 300 and 1,000 nM, respectively. CRIC3 is more potent than the other derivatives, as its maximal effect observed was at 10 nM, which is in the range of eotaxin as previously shown[11]. When eosinophils are treated with 100 nM CRIC3 prior to application to the migration chamber, it dramatically decreases the migratory response towards CCL11 close to medium response (FIG. 4b).

CRIC3 Induces a Functional Desensitization of CCR3

Figure 5A:
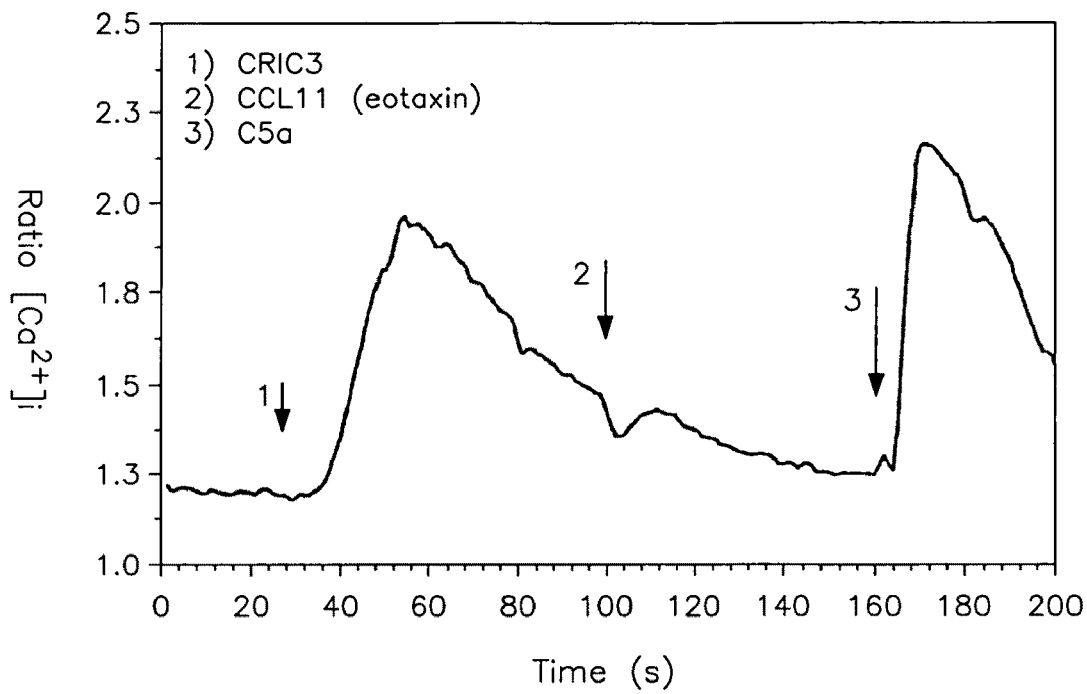
FIG. 5: CRIC3 induces a functional desensitization of CCR3.
Figure 5B:
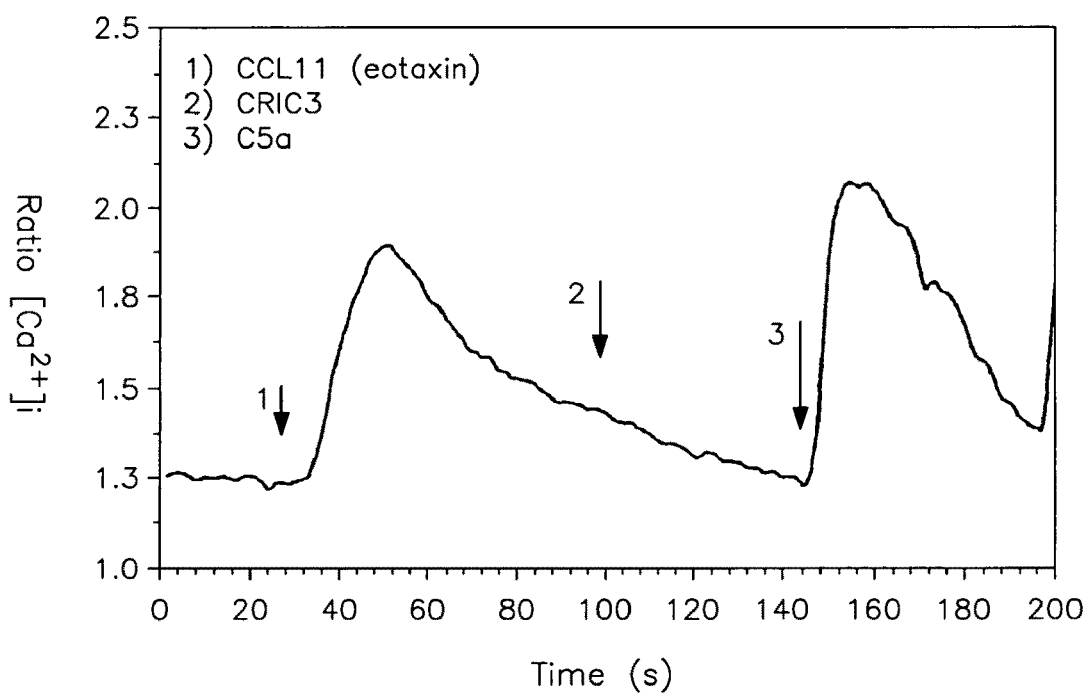
Figure 5C:
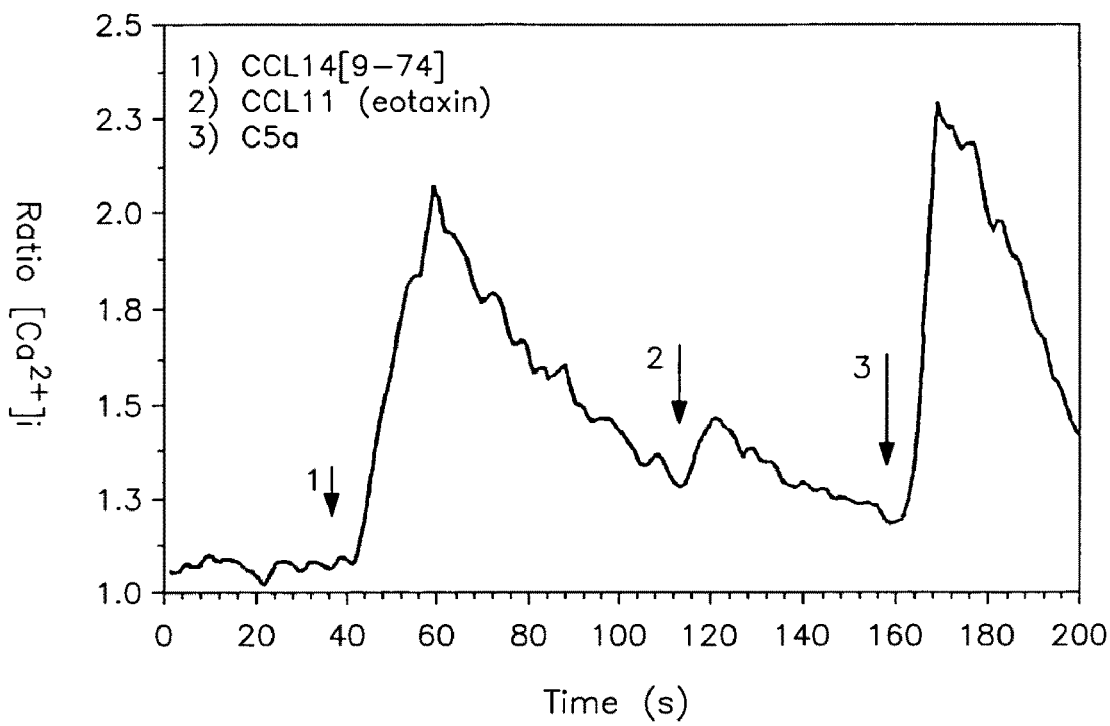
Figure 5D:
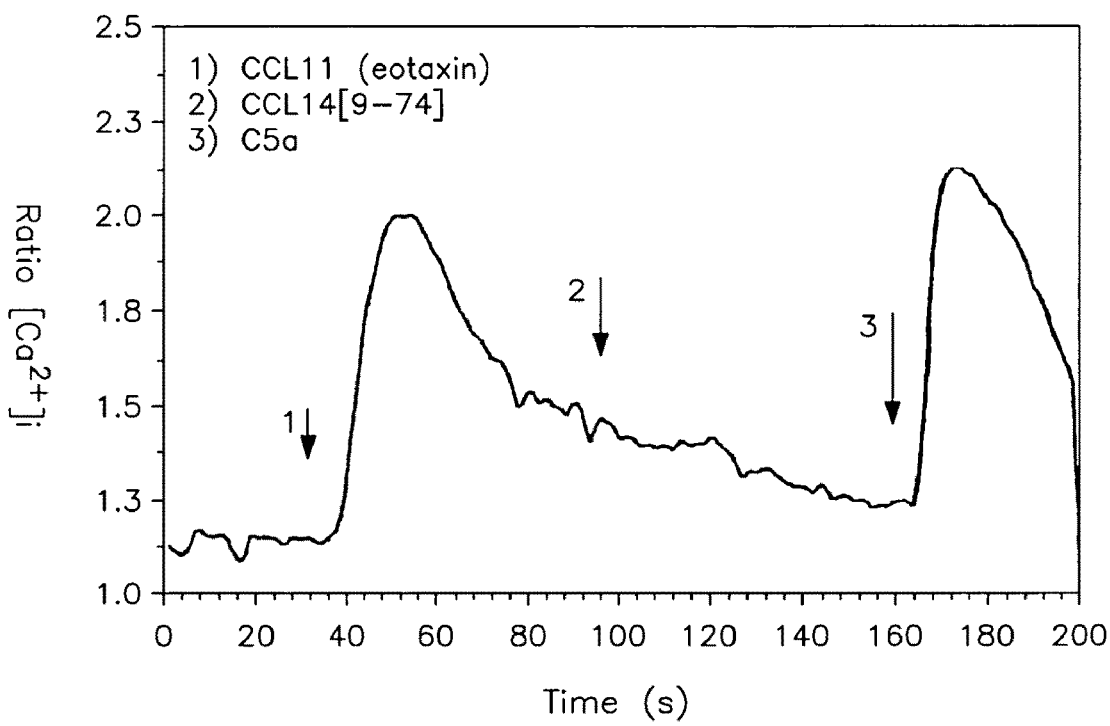
Figure 5E:
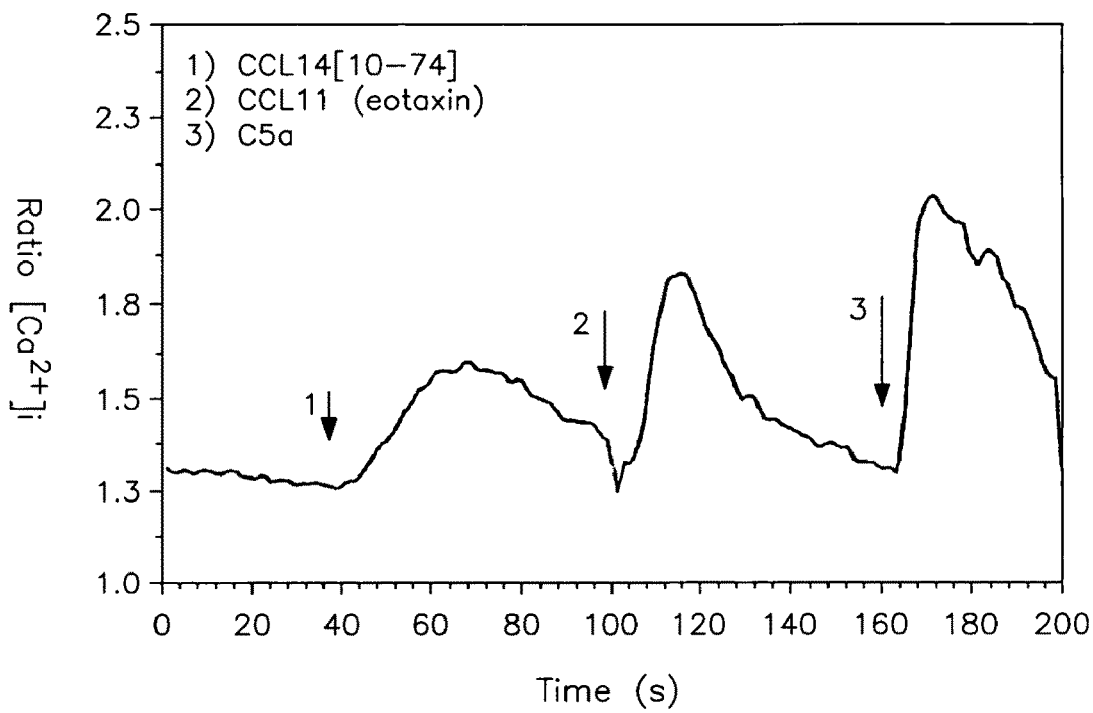
Figure 5F:
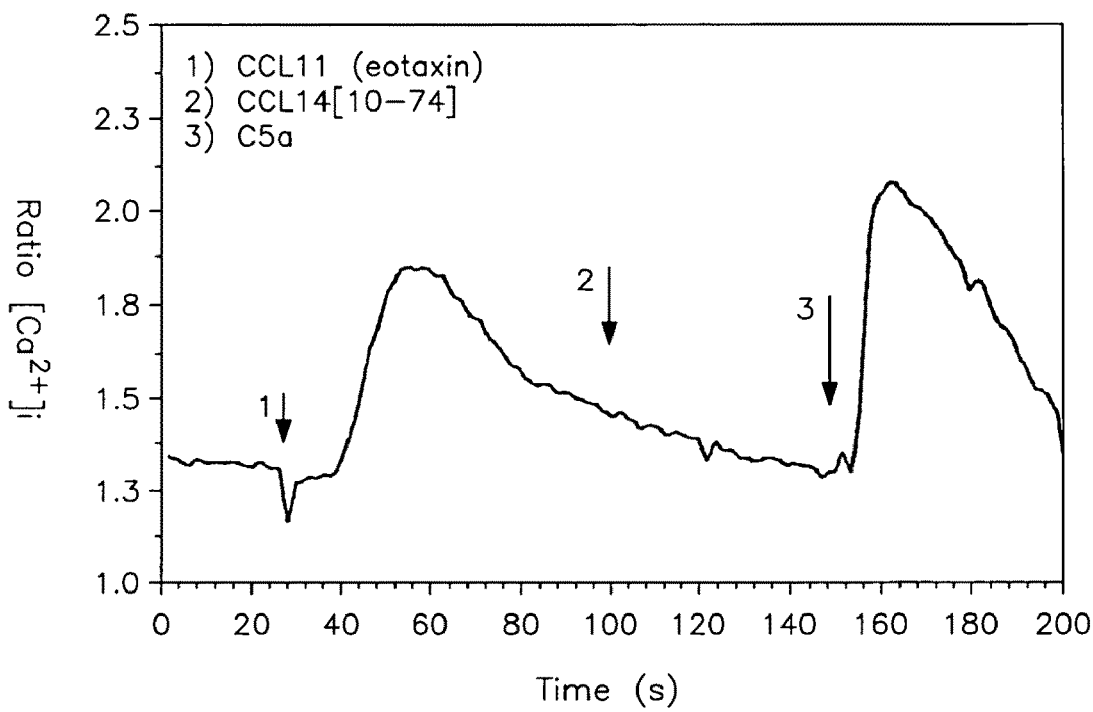

CCL11 induced $[Ca^{2+}]_i$ changes in human eosinophils are exclusively mediated via CCR3[39]. In order to study the potential of the active CCL14 derivatives to desensitize CCR3, heterologous desensitization experiments were performed with the most active CCL14 derivatives and CCL11. Stimulation of eosinophils with CCL14[9-74] or CRIC3 at $10^{-7}$ M completely desensitized the cells to CCL11 at the same dose (FIGS. 5a and c). The less active form CCL14[10-74] did virtually not desensitize eotaxin at equal doses (FIG. 5e), which is in agreement with the results obtained for the release of ROS and the moderate CCR3 internalization after preincubation with this ligand. Stimulation of eosinophils with CCL11 completely desensitized the active CCL14 derivatives in all experiments performed (FIGS. 5b, d, and f), indicating that all donors used did not express functional CCR1. These results demonstrate that CRIC3 induces a functional desensitization of CCR3 and makes it resistant to its activation by CCL11.

CRIC3 is resistant to CD26/DPP IV processing.

Figure 6A:
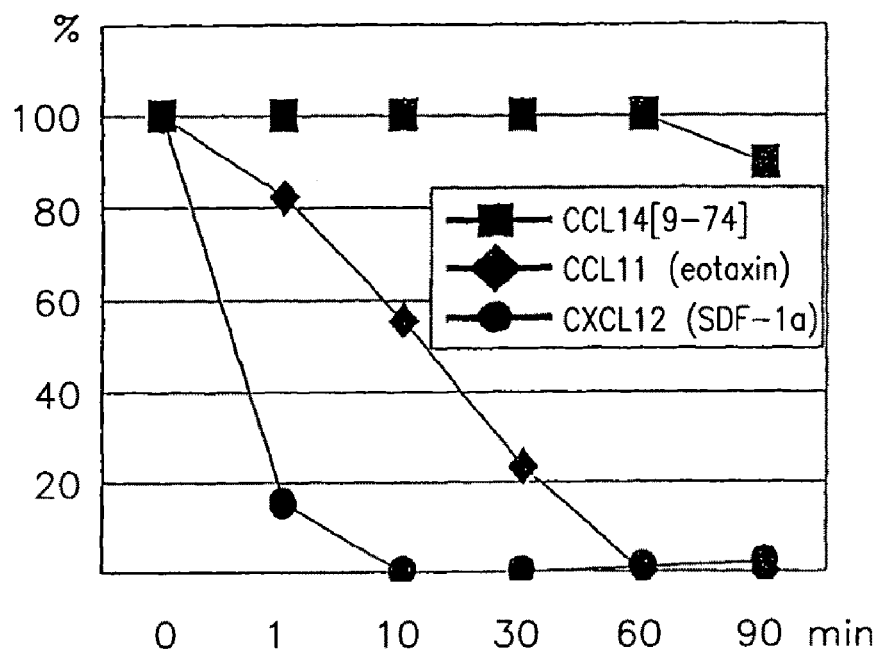
FIG. 6: CRIC3 is not processed by CD26/DPP IV.
Figure 6B:
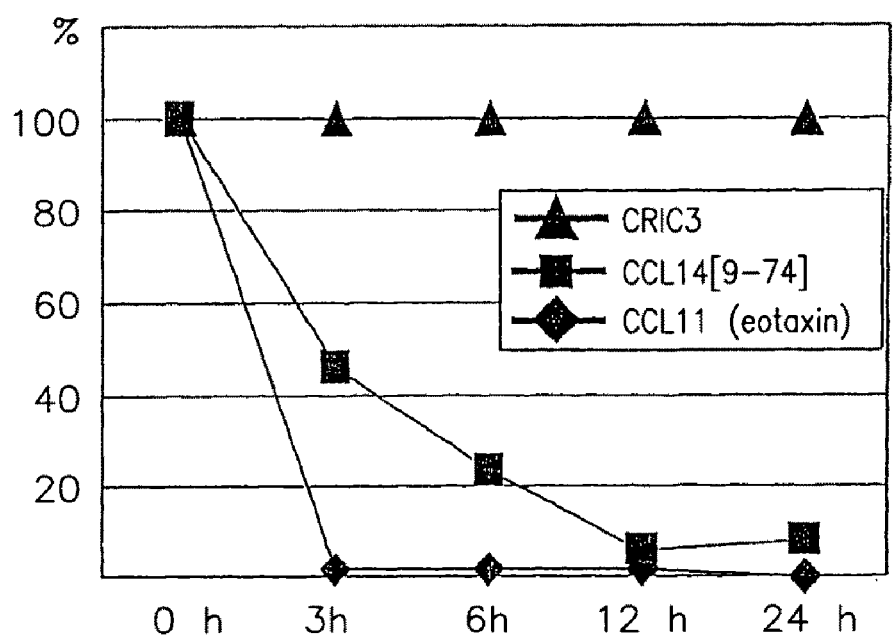
Figure 6C:
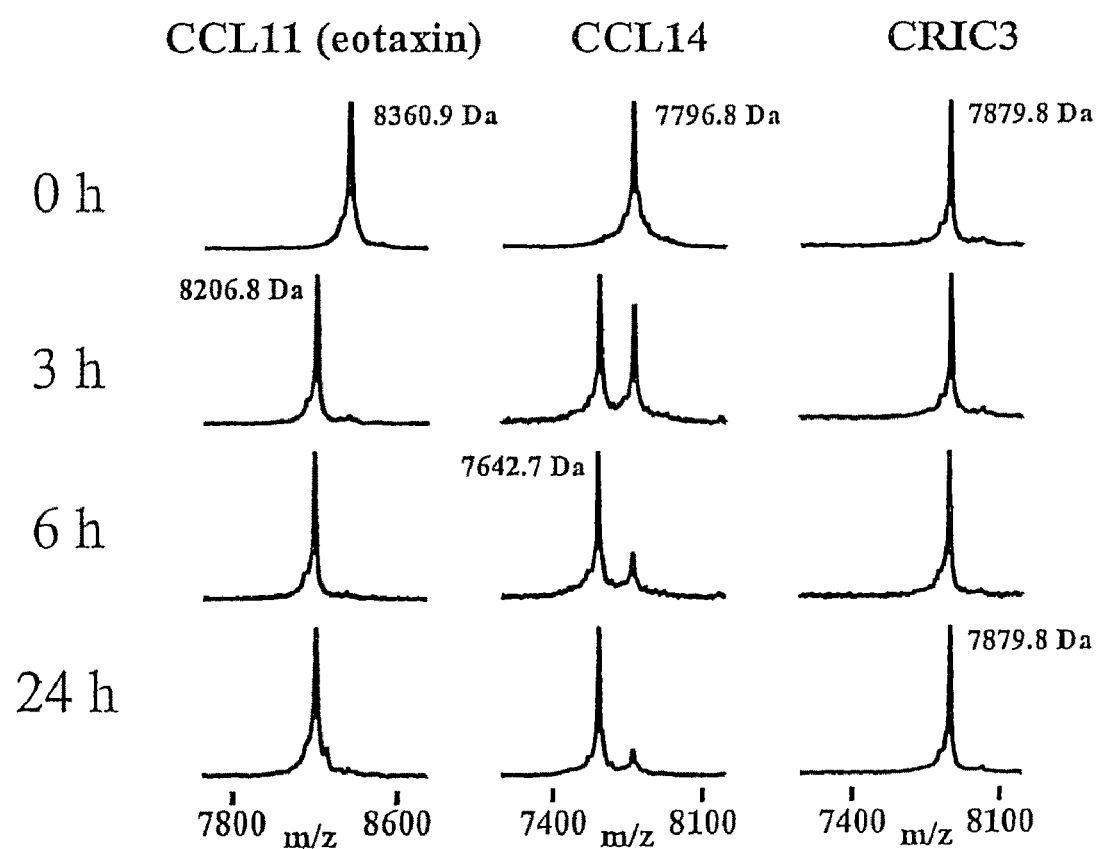

CD26/DPP IV processing of CCL11, CCL14[9-74] and CRIC3 was analyzed in vitro, essentially as described by Lambeir et al.[34]. First the amount of enzyme applied was optimized to give a kinetic profile for CCL11 and CXCL12 comparable to that previously reported (FIG. 6a). CXCL12 was completely processed within 10 min and CCL11[1-74] was fully converted into CCL11[3-74] after 1 h at 37° C. Using these conditions, the processing of CCL14[9-74] was followed over time in a similar fashion. Although significantly slower than for CCL11 and CXCL12, a virtually complete conversion of CCL14[9-74] into CCL14[11-74] was achieved within 12 h. In contrast to these chemokines CRIC3 remained completely resistant to CD26/DPP IV treatment after 24 h (FIGS. 6b and c) and even after 90 h of incubation (not shown).

Figure 7B:
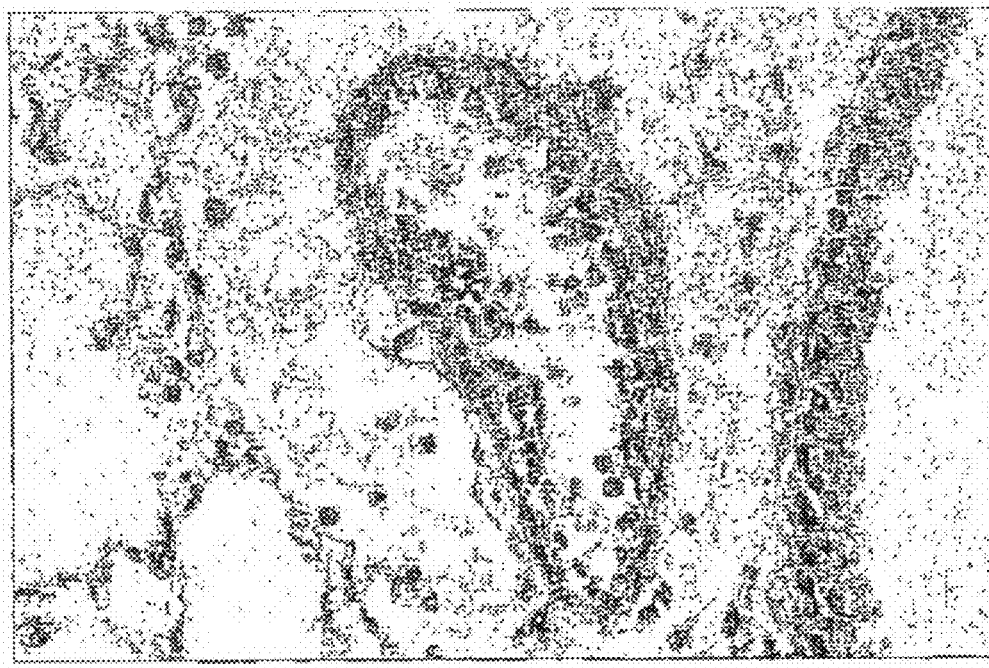
FIG. 7: CRIC3 prevented slightly the influx of eosinophils into the lung tissue of OVA-sensitized mice.
Figure 7A:
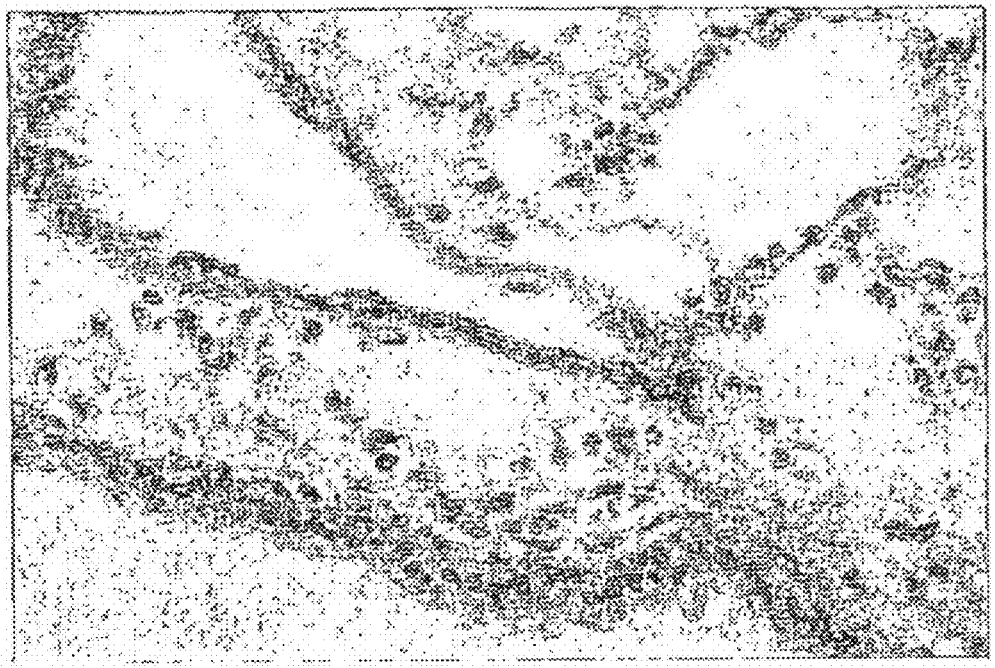
Figure 8:
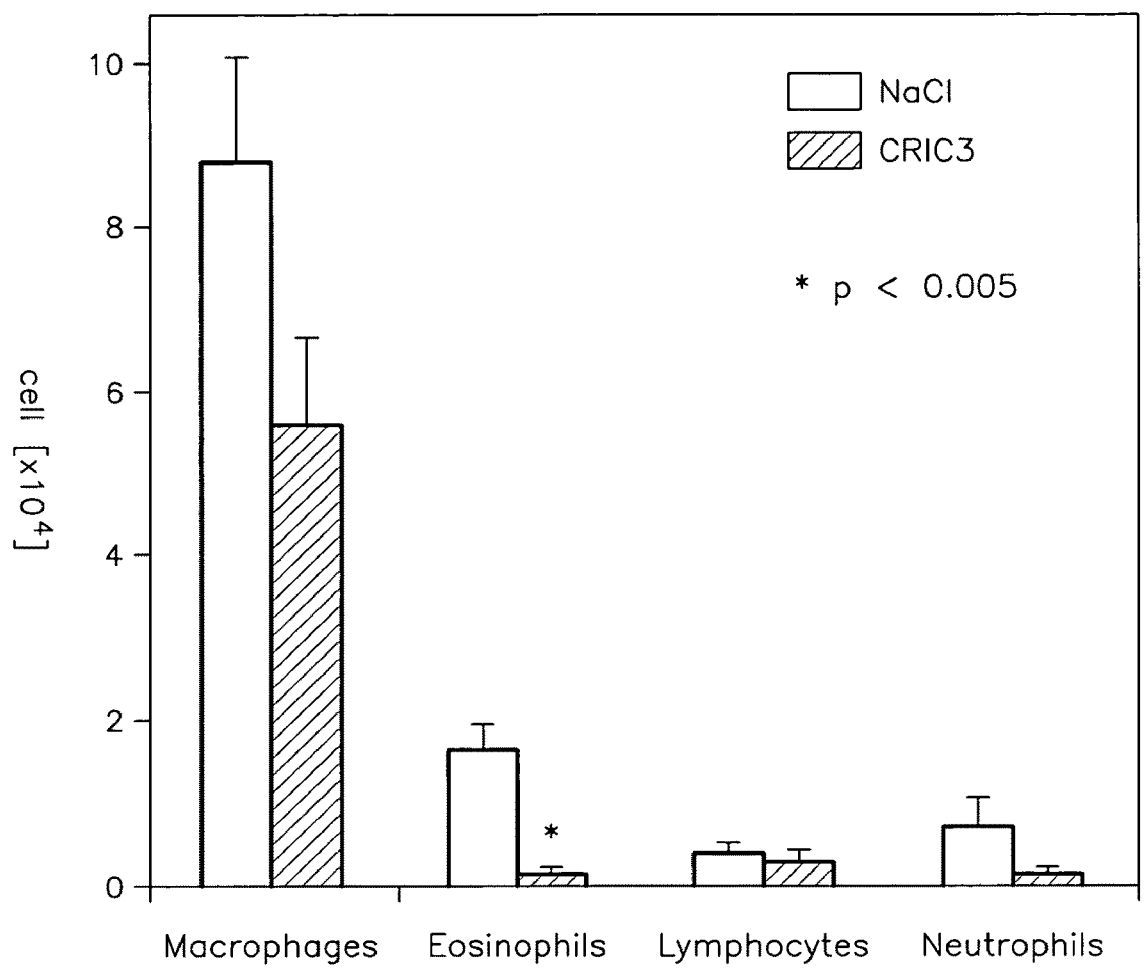
FIG. 8: CRIC3 prevented the influx of eosinophils into the BALF in OVA-sensitized mice.

CRIC3 is an effective inhibitor of eosinophil infiltration in a murine model of allergic lung inflammation To test the hypothesis that CRIC3 may influence the influx of eosinophils in vivo a murine model of allergic asthma was used. The intravenous application of 10 nM/kg CRIC3 30 min before and 3 h and 8 h after allergen aerosol provocation significantly reduced the infiltration of eosinophils into the airways in comparison to the saline treated control group. Eosinophil infiltration into the lung tissue was demonstrated by standard staining procedures and was clearly reduced in the CRIC3 treated animals (FIGS. 7a and b). For quantification of the effect on inflammation, differential cell counts were performed on cytospins of BALF. Application of CRIC3 significantly reduced the influx of eosinophils into the airways when compared to the saline treated group (0.2 vs. $1.62 \times 10^4$ cells per ml BALF, p<0.005) (FIG. 8).

Discussion

Recent discoveries on the immunological mechanisms of asthma have markedly altered our understanding of this common respiratory disorder. These insights have been gained during a persistent period of rising disease incidence and severity and are now being applied to develop improved therapies[40]. Whereas steroids are one of the most potent and broad-spectrum drug for the therapy of the inflammatory phase in asthma[41], many new concepts focus to block a specific cytokine, chemokine or cell type in the expectance to reduce side effects and to be more successful. In this context humanized antibodies, e.g. against IL-5[42], and chemokine receptor antagonist have been developed to hinder the invasion of leukocytes to the site of inflammation[43]. Whereas most of these anti-inflammatory strategies act on the target cells after they migrated to the site of inflammation, a concept is proposed in which the cellular recruitment is prevented by inactivation of the chemokine receptor before cells leave the blood vessels. Herein it is demonstrated that the CD26-resistant inactivator of CCR3, CRIC3, which derives from the recently identified chemokine CCL14[9-74] is a potent ligand of the human CC chemokine receptor CCR3 and able to prevent eosinophil invasion into the lung in a murine model of allergic asthma.

Recently, the importance of the CC chemokine receptor CCR3 in allergic asthma has been highlighted. This receptor is expressed constitutively or upon activation of cytokines on eosinophils, Th2 cells, basophils and mast cells[17-20]. All these cells contribute to the inflammatory infiltrate in allergic asthma[1]. The deletion of the CCR3 locus in the germ line of mice gave new insight in the role of this receptor for the trafficking of different immune cells into the lung[23;24]. These studies showed in a model of allergen-induced airway inflammation, that allergen challenge results in subendothelial trapping of eosinophils in CCR3 deficient mice, while wild-type controls had an impressive infiltration of the lung accompanied by lymphocytes, which were both not found in CCR3−/− mice. Moreover, the CCR3-deficient mice are completely protected from allergen-induced AHR, if the epicutaneous route is used for sensitization instead of the intraperitoneal, underlining the relevance of CCR3 in several phases of asthma[23;24].

In the past, the naturally occurring mature form of CCL14 were isolated, circulating in nanomolar levels in the plasma, exhibiting minimal biological effects[26]. Further investigations led to the identification of the N-terminal truncated form CCL14[9-74], which can be generated in nature[28;44]. This variant was shown to be a good agonist of CCR3. In this study, it was our aim to design a ligand of CCR3 leading to its inactivation. Therefore, several forms of CCL14 with different N-terminal length were synthesized. However, screening of the variants for their potential to inhibit the respiratory burst induced by CCL11, did not result in the identification of an antagonist. As several studies have demonstrated, that modification of the N-terminal amino acid reveal dramatic changes in the activity of chemokines, the ultimate amino acid of the most active variant were replaced. For this replacement, nonanoic acid was used as NNY-RANTES was recently shown to be a more potent inhibitor of HIV infection than AOP-RANTES[45].

Here it is shown that the modified variant of CCL14, CRIC3 acts as a high-affinity agonist of CCR3, as only human eosinophils were used expressing CCR3 but not CCR1 (see results). Screening of different variants of CCL14 using an assay for the respiratory burst revealed that CRIC3 is a highly potent agonist of CCR3 identical to CCL11. In addition, this modified peptide induces surface internalization of CCR3 as effective as CCL11. Performing chemotaxis assays with eosinophils revealed an activity profile being very similar to CCL11[11]. Furthermore, in desensitization experiments the usage of CCR3 by CRIC3 was confirmed which makes it resistant to activation by CCL11.

As expected from the amino acid sequence it was demonstrated that CRIC3 was not degraded by DPP IV/CD26. This is a relevant difference in comparison to CCL11. The latter was processed rapidly in its inactivated form, CCL11[3-74]. This processing reduces the interaction of CCL11 with CCR3[46]. CD26/DPP IV occurs in highly active levels in human plasma and is also well known as a widely distributed cell-surface glycoprotein[47;48]. The plasma stability of other peptides such as GLP-1, a potent insulinotropic hormone expressed by intestinal L-cells, have been shown to depend on degradation by CD26/DPP IV[49]. The anti-diabetogenic effect of GLP-1 was clearly demonstrated in patients with type-II diabetes[50] and therefore it is not surprising, that several antagonists of CD26/DPP IV are already launched for clinical trials[51]. However, as a suppressor of CCR3 induced inflammation, the CD26-resistant inactivator of CCR3, CRIC3, is most likely superior to a combination of CCL11 and an inhibitor of the broad spectrum enzyme DPP IV/CD26. The most potent CCR3 peptide antagonist yet described, I-Tac/$E_0$H1 contains the eight N-terminal amino acids of CXCL11 (I-TAC)[53]. As CXCL11 is efficiently cleaved by CD26/DPP IV[52], I-Tac/$E_0$H1 is likely to share a similar fate, resulting in a short plasma half-life.

The therapeutic use of chemokines or their derivatives with antagonistic or agonistic properties such as Met-RANTES 54, AOP-RANTES 55, or NNY-RANTES[5]6 has been intensively discussed in the literature especially for the inhibition of HIV infection[57]. The treatment of asthma is one rationale for the development of CCR3 antagonists like Met-RANTES or ITAC/$E_0$H1[53]. Other modifications like the replacement of the first amino-terminal residue by aminooxypentane, which was done to create an antagonist[55] revealed at least a partial agonist[33]. Besides peptides, small molecular weight compounds are also considered as potential drugs for the blockade of chemokine receptors.

Since the latter compounds derived from piperazine and piperidine may exhibit unexpected side effects (particularly heart and central nervous system), peptide ligands inactivating chemokine receptors represent a respectable alternative due to a better tolerance.

Based on our observations, it is not devious to propose the use of full agonists for the treatment of disease. Many antagonists used in other medical areas have an intrinsic activity, which is well tolerated. There are also agonists on the market, which are applied to induce inhibitory effects, such as LHRH analogs, which are used to down-regulate hormone release[58]. Therefore, the present invention discloses a method of an agonistic receptor inactivator mediating its effects through desensitization and internalization. CRIC3 might be applied into a defined body compartment to activate cells at sites were they are not harmful and thereby rendering them insensitive to further activation through the same receptor. This inactivation is the result of desensitization depending most likely on the uncoupling of the receptor from heterotrimeric G proteins in response to receptor phosphorylation and the internalization of receptors to intracellular membranous compartments[59].

To prove whether CRIC3 is able to block the infiltration of $CCR3^+$ cells into the lung tissue we used a murine model of allergic asthma. Intravenous administration of CRIC3 prior and after allergen challenge was well tolerated without any side effects. Remarkably, the number of eosinophils in the BALF as well as in the lung tissue dramatically decreased in the CRIC3-treated group. Therefore, a blockade of the migration towards the inflammatory focus is the result of the unresponsiveness. The blood represents the ideal compartment for application of such a CD26-resistant inactivator of CCR3, as generated toxic substances like ROS accumulate much slower than directly in the inflamed tissues. Other forms of application than systemic administration might cause adverse events. Therefore, peptides would be interesting candidates as they are mainly administered parenteral and are usually highly specific and have therefore relatively low systemic toxicity 60. It should also be mentioned that agonists such as CRIC3 have to be given at much lower doses and less frequently to desensitize the effector cells than antagonists like Met-RANTES to block cellular responsiveness[61], as down-regulation of surface receptors might prolong the effects of agonists in comparison to antagonists. The reason that we were not able to prevent the influx of all eosinophils into the lung (quantified by BALF analysis) may be due to the application and provocation protocol in our study. Further studies are necessary for pharmacokinetic evaluation and to show the effect on AHR. Nevertheless, we could clearly demonstrate that CRIC3 principally acts in vivo.

Up to date, peptides with agonistic activities have not been proposed for the treatment of CCR3 driven pathologies. As shown by our study, CRIC3 represents such a candidate. Therefore, CRIC3 could be useful in diseases which are dominated by effects depending on CCR3, but also in diseases with a broader spectrum of chemokine receptors involved, which might be true for asthma. In accordance with this, the broad-spectrum chemokine receptor antagonist vMI-PII has been shown to be more effective in a model of spinal cord injury with posttraumatic inflammation than the more specific antagonist MCP-1(9-76)[62;63]. The results of our study implicate the new concept to generate an inactivating agonist which is resistant to degradation by serum and tissue peptidases. As a consequence of the inactivation of receptors by an agonist, the recruitment of eosinophils, basophiles, and $Th_2$ cells into tissues could be prevented in CCR3-driven pathologies as suggested by our study.

Abbreviations

CCL, CC chemokine ligand; CRIC3, n-nonanoyl-CCL14 [10-14]; bis-NNY-CCL14[10-74], Bis-n-nonanoyl-CCL14 [10-74]; RANTES, regulation upon activation and T cell secreted; BALF, bronchoalveolar lavage fluid; AHR, airway hyper responsiveness; OVA, ovalbumin

FIG. 1:

Alignment of N-terminal sequences of CCL14 derivatives and CCL11.

The cleavage motif for CD26/DPP IV of CCL14[9-74] and CCL11 (eotaxin) is marked in gray.

FIG. 2:

CRIC3 induces the release of reactive oxygen species (ROS) from human eosinophils with more potency than CCL11.

The release of ROS was measured using lucigenin-dependent chemiluminescence. Human eosinophils were stimulated with different concentrations of the indicated chemokine. Data (n=7) are expressed as relative ROS release that is expressed as the ratio of stimulus-stimulated and medium-stimulated cells.

FIG. 3:

CRIC3 induces an internalization of CCR3 from human eosinophils in the same range than CCL11.

Human eosinophils were treated with the indicated CCL14 derivatives ($10^{-7}$ M) and CCL11 ($10^{-7}$ M), respectively, for 30 min at 37° C. Thereafter cells were stained with anti-CCR3 mAb and analyzed by flow cytometry. A: Data (n=4) are expressed as the mean±SEM of relative fluorescence intensity as described in Materials and Methods. B: Histogram analysis of one representative experiment shown in FIG. A. Bold line, anti-CCR3 staining before chemokine treatment; dotted line, isotype control; broken line, anti-CCR3 staining after chemokine treatment. C: Cells were incubated with the indicated chemokine ($10^{-7}$ M), at 37° C., 4° C. or pretreated with PAO. Data (n=4) are expressed as the mean±SEM of relative fluorescence intensity.

FIG. 4:

CRIC3 induces chemotaxis of eosinophils but also inhibits CCL11.

A) CCL14 derivatives induce in vitro chemotaxis of human eosinophils. Numbers of migrating cells per five high power. (×1000) fields are given. One out of three similar experiments performed with cells from different donors is shown. B) Pretreatment of eosinophils with 100 nM CRIC3 15 min before loading to the chemotaxis chamber dramatically inhibits CCL11 induced migration.

FIG. 5:

CRIC3 induces a functional desensitization of CCR3.

Human eosinophils were loaded with Fura-2 and $[Ca^{2+}]_i$ was measured using spectrofluometry. Cells were stimulated with the indicated chemokine ($10^{-7}$ M) and the anaphylatoxin C5a ($10^{-8}$ M). Data are expressed as original plot of one representative experiment out of five.

FIG. 6:

CRIC3 is not processed by CD26/DPP IV.

A and B) CCL11/eotaxin[1-74], CXCL12/SDF-1α[22-89], and CCL14/HCC-1[9-74] (10 μM each) were incubated for the indicated times with porcine kidney CD26/DPP IV as described in Materials and Methods and analyzed using mass spectrometry. Processing was calculated as amount of full-length chemokine related to total amount of the full-length and processed forms as defined by the peak heights. C) Partial MALDI mass spectrometry spectra of chemokines after incubation for different times. The relative molecular masses of unprocessed chemokines are indicated on the right side of the peaks, and of processed (minus 2 N-terminal amino acids) on the left.

FIG. 7.

CRIC3 prevents the diapedesis of eosinophils into the lung tissue of OVA-sensitized mice. The photographs represent the reduced diapedesis of eosinophils being arrested on the venule endothelium in CRIC3-treated mice (A), in comparison to the saline-treated group having a marked peribronchial infiltration primarily consisting of eosinophils (B). Original magnification 630×.

FIG. 8.

CRIC3 prevents the migration of eosinophils into the BALF of OVA-challenged mice. OVA-challenged mice were treated with CRIC3 (3×10 nmol/kg) or saline, respectively. Cell composition in BALF 24 h after allergen challenge was analyzed differentiating 500 cells per cytospin and expressed as total cell numbers.

REFERENCES

1. Busse, W. W. and R. F. Lemanske. 2001. Review Articles: Advances in Immunology: Asthma. *N. Engl. J. Med.* 344: 350-362.
2. Barnes, P. J., K. F. Chung, and C. P. Page. 1998. Inflammatory mediators of asthma: an update. *Pharmacol. Rev.* 50:515-596.
3. Gleich, G. J. 2000. Mechanisms of eosinophil-associated inflammation. *J. Allergy Clin. Immunol.* 105:651-663.
4. Wardlaw, A. J., S. Dunnette, G. J. Gleich, J. V. Collins, and A. B. Kay. 1988. Eosinophils and mast cells in bronchoalveolar lavage in subjects with mild asthma. Relationship to bronchial hyperreactivity. *Am. Rev. Respir. Dis.* 137:62-69.
5. Robinson, D. S., Q. Hamid, S. Ying, A. Tsicopoulos, J. Barkans, A. M. Bentley, C. Corrigan, S. R. Durham, and A. B. Kay. 1992. Predominant TH2-like bronchoalveolar T-lymphocyte population in atopic asthma. *N. Engl. J. Med.* 326:298-304.
6. Springer, T. A. 1994. Traffic signals for lymphocyte recirculation and leukocyte emigration: the multistep paradigm. *Cell* 76:301-314.
7. Butcher, E. C. and L. J. Picker. 1996. Lymphocyte homing and homeostasis. *Science* 272:60-66.
8. Worthylake, R. A. and K. Burridge. 2001. Leukocyte transendothelial migration: orchestrating the underlying molecular machinery. *Curr. Opin. Cell Biol.* 13:569-577.
9. Griffiths Johnson, D. A., P. D. Collins, A. G. Rossi, P. J. Jose, and T. J. Williams. 1993. The chemokine, eotaxin, activates guinea-pig eosinophils in vitro and causes their accumulation into the lung in vivo. *Biochem. Biophys. Res. Commun.* 197:1167-1172.
10. Ponath, P. D., S. Qin, D. J. Ringler, I. Clark Lewis, J. Wang, N. Kassam, H. Smith, X. Shi, J. A. Gonzalo, W. Newman, J. C. Gutierrez Ramos, and C. R. Mackay. 1996. Cloning of the human eosinophil chemoattractant, eotaxin. Expression, receptor binding, and functional properties suggest a mechanism for the selective recruitment of eosinophils. *J. Clin. Invest.* 97:604-612.
11. Forssmann, U., M. Uguccioni, P. Loetscher, C. A. Dahinden, H. Langen, M. Thelen, and M. Baggiolini. 1997. Eotaxin-2, a novel CC chemokine that is selective for the chemokine receptor CCR3, and acts like eotaxin on human eosinophil and basophil leukocytes. *J. Exp. Med.* 185: 2171-2176.
12. Shinkai, A., H. Yoshisue, M. Koike, E. Shoji, S. Nakagawa, A. Saito, T. Takeda, S. Imabeppu, Y. Kato, N. Hanai, H. Anazawa, T. Kuga, and T. Nishi. 1999. A novel human CC chemokine, eotaxin-3, which is expressed in IL-4-stimulated vascular endothelial cells, exhibits potent activity toward eosinophils. *J. Immunol.* 163:1602-1610.
13. Elsner, J., A. Kapp, J. C. Virchow, Jr., and W. Luttmann. 2001. Eosinophils: Quo vadis? The role of eosinophils in the chemokine network of allergy. *Mod. Asp. Immunobiol.* 2:18-24.

14. Forssmann, U., H. J. Magert, K. Adermann, S. E. Escher, and W. G. Forssmann. 2001. Hemofiltrate CC chemokines with unique biochemical properties: HCC-1/CCL14a and HCC-2/CCL15. *J. Leukoc. Biol.* 70:357-366.
15. Ying, S., Q. Meng, K. Zeibecoglou, D. S. Robinson, A. Macfarlane, M. Humbert, and A. B. Kay. 1999. Eosinophil Chemotactic Chemokines (Eotaxin, Eotaxin-2, RANTES, Monocyte Chemoattractant Protein-3 (MCP-3), and MCP-4), and C-C Chemokine Receptor 3 Expression in Bronchial Biopsies from Atopic and Nonatopic (Intrinsic) Asthmatics. *J. Immunol.* 163:6321-6329.
16. Lilly, C. M., H. Nakamura, O. I. Belostotsky, K. J. Haley, E. A. Garcia-Zepeda, A. D. Luster, and E. Israel. 2001. Eotaxin expression after segmental allergen challenge in subjects with atopic asthma. *Am. J. Respir. Crit. Care Med.* 163:1669-1675.
17. Ponath, P. D., S. Qin, T. W. Post, J. Wang, L. Wu, N. P. Gerard, W. Newman, C. Gerard, and C. R. Mackay. 1996. Molecular cloning and characterization of a human eotaxin receptor expressed selectively on eosinophils. *J. Exp. Med.* 183:2437-2448.
18. Ochi, H., W. M. Hirani, Q. Yuan, D. S. Friend, K. F. Austen, and J. A. Boyce. 1999. T helper cell type 2 cytokine-mediated comitogenic responses and CCR3 expression during differentiation of human mast cells In vitro. *J. Exp. Med.* 190:267-280.
19. Uguccioni, M., C. R. Mackay, B. Ochensberger, P. Loetscher, S. Rhis, G. J. LaRosa, P. Rao, P. D. Ponath, M. Baggiolini, and C. A. Dahinden. 1997. High Expression of the Chemokine Receptor CCR3 in Human Blood Basophils. Role in activation by eotaxin, mcp-4, and other chemokines. *J. Clin. Invest.* 100:1137-1143.
20. Sallusto, F., C. R. Mackay, and A. Lanzavecchia. 1997. Selective expression of the eotaxin receptor CCR3 by human T helper 2 cells. *Science* 277:2005-2007.
21. Gerber, B. O., M. P. Zanni, M. Uguccioni, M. Loetscher, C. R. Mackay, W. J. Pichler, N. Yawalkar, M. Baggiolini, and B. Moser. 1997. Functional expression of the eotaxin receptor CCR3 in T lymphocytes co-localizing with eosinophils. *Curr. Biol.* 7:836-843.
22. Gonzalo, J. A., C. M. Lloyd, D. Wen, J. P. Albar, T. N. Wells, A. Proudfoot, C. Martinez-A, M. Dorf, T. Bjerke, A. J. Coyle, and J. C. Gutierrez-Ramos. 1998. The coordinated action of CC chemokines in the lung orchestrates allergic inflammation and airway hyperresponsiveness. *J. Exp. Med.* 188:157-167.
23. Humbles, A. A., B. Lu, D. S. Friend, S. Okinaga, J. Lora, A. Al Garawi, T. R. Martin, N. P. Gerard, and C. Gerard. 2002. The murine CCR3 receptor regulates both the role of eosinophils and mast cells in allergen-induced airway inflammation and hyperresponsiveness. *Proc. Natl. Acad. Sci. U.S.A* 99:1479-1484.
24. Ma, W., P. J. Bryce, A. A. Humbles, D. Laouini, A. Yalcindag, H. Alenius, D. S. Friend, H. C. Oettgen, C. Gerard, and R. S. Geha. 2002. CCR3 is essential for skin eosinophilia and airway hyperresponsiveness in a murine model of allergic skin inflammation. *J. Clin. Invest* 109:621-628.
25. Bertrand, C. P. and P. D. Ponath. 2000. CCR3 blockade as a new therapy for asthma. *Expert. Opin. Investig. Drugs* 9:43-52.
26. Schulz-Knappe, P., H. J. Magert, B. Dewald, M. Meyer, Y. Cetin, M. Kubbies, J. Tomeczkowski, K. Kirchhoff, M. Raida, and K. Adermann. 1996. HCC-1, a novel chemokine from human plasma. *J. Exp. Med.* 183:295-299.
27. Tsou, C. L., R. P. Gladue, L. A. Carroll, T. Paradis, J. G. Boyd, R. T. Nelson, K. Neote, and I. F. Charo. 1998. Identification of C-C chemokine receptor 1 (CCR1) as the monocyte hemofiltrate C-C chemokine (HCC)-1 receptor. *J. Exp. Med.* 188:603-608.
28. Detheux, M., L. Standker, J. Vakili, J. Munch, U. Forssmann, K. Adermann, S. Pohlmann, G. Vassart, F. Kirchhoff, M. Parmentier, and W. G. Forssmann. 2000. Natural proteolytic processing of hemofiltrate CC chemokine 1 generates a potent CC chemokine receptor (CCR)1 and CCR5 agonist with anti-HIV properties. *J. Exp. Med.* 192:1501-1508.
29. Mentlein, R. 1999. Dipeptidyl-peptidase IV (CD26)—role in the inactivation of regulatory peptides. *Regul. Pept.* 85:9-24.
30. Loetscher, P. and I. Clark-Lewis. 2001. Agonistic and antagonistic activities of chemokines. *J Leukoc. Biol.* 69:881-884.
31. Escher, S. E., E. Kluver, and K. Adermann. 2002. Fmoc based synthesis of the human CC chemokine CCL14/HCC-1 by SPPS and native chemical ligation. *Letters in Peptide Science.*
32. Dulkys, Y., C. Kluthe, T. Buschermohle, I. Barg, S. Knoss, A. Kapp, A. E. Proudfoot, and J. Elsner. 2001. IL-3 Induces Down-Regulation of CCR3 Protein and mRNA in Human Eosinophils. *J. Immunol.* 167:3443-3453.
33. Elsner, J., M. Mack, H. Bruhl, Y. Dulkys, D. Kimmig, G. Simmons, P. R. Clapham, D. Schlondorff, A. Kapp, T. N. Wells, and A. E. Proudfoot. 2000. Differential Activation of CC Chemokine Receptors by AOP-RANTES. *J. Biol. Chem.* 275:7787-7794.
34. Lambeir, A. M., P. Proost, C. Durinx, G. Bal, K. Senten, K. Augustyns, S. Scharpe, J. Van Damme, and M. De, I. 2001. Kinetic investigation of chemokine truncation by CD26/dipeptidyl peptidase IV reveals a striking selectivity within the chemokine family. *J Biol. Chem.* 276:29839-29845.
35. Braun, A., E. Appel, R. Baruch, U. Herz, V. Botchkarev, R. Paus, C. Brodie, and H. Renz. 1998. Role of nerve growth factor in a mouse model of allergic airway inflammation and asthma. *Eur. J. Immunol.* 28:3240-3251.
36. Munch, J., L. Standker, S. Pohlmann, F. Baribaud, A. Papkalla, O. Rosorius, R. Stauber, G. Sass, N. Heveker, K. Adermann, S. Escher, E. Kluver, R. W. Doms, W. G. Forssmann, and F. Kirchhoff. 2002. Hemofiltrate CC chemokine 1[9-74] causes effective internalization of CCR5 and is a potent inhibitor of R5-tropic human immunodeficiency virus type 1 strains in primary T cells and macrophages. *Antimicrob. Agents Chemother.* 46:982-990.
37. Elsner, J., R. Hochstetter, D. Kimmig, and A. Kapp. 1996. Human eotaxin represents a potent activator of the respiratory burst of human eosinophils. *Eur. J. Immunol.* 26:1919-1925.
38. Roettger, B. F., R. U. Rentsch, D. Pinon, E. Holicky, E. Hadac, J. M. Larkin, and L. J. Miller. 1995. Dual pathways of internalization of the cholecystokinin receptor. *J. Cell Biol.* 128:1029-1041.
39. Heath, H., S. Qin, P. Rao, L. Wu, G. LaRosa, N. Kassam, P. D. Ponath, and C. R. Mackay. 1997. Chemokine receptor usage by human eosinophils. The importance of CCR3 demonstrated using an antagonistic monoclonal antibody. *J. Clin. Invest.* 99:178-184.
40. Corry, D. B. 2002. Emerging immune targets for the therapy of allergic asthma. *Nature Rev.* 1:55-64.
41. Barnes, P. J. 2001. Molecular mechanisms of corticosteroids in allergic diseases. *Allergy* 56:928-936.
42. Leckie, M. J., A. ten Brinke, J. Khan, Z. Diamant, B. J. O'Connor, C. M. Walls, A. K. Mathur, H. C. Cowley, K. F. Chung, R. Djukanovic, T. T. Hansel, S. T. Holgate, P. J. Sterk, and P. J. Barnes. 2000. Effects of an interleukin-5 blocking monoclonal antibody on eosinophils, airway hyper-responsiveness, and the late asthmatic response. *Lancet* 356:2144-2148.
43. Proudfoot, A. E. 2002. Chemokine receptors: multifaceted therapeutic targets. *Nature Rev. Immunol.* 2:106-115.
44. Vakili, J., L. Standker, M. Detheux, G. Vassart, W. G. Forssmann, and M. Parmentier. 2001. Urokinase plasminogen activator and plasmin efficiently convert hemofiltrate CC chemokine 1 into its active. *J Immunol* 167:3406-3413.
45. Sabbe, R., G. R. Picchio, C. Pastore, O. Chaloin, O. Hartley, R. Offord, and D. E. Mosier. 2001. Donor- and ligand-dependent differences in C-C chemokine receptor 5 reexpression. *J. Virol.* 75:661-671.
46. Struyf, S., P. Proost, D. Schols, E. De Clercq, G. Opdenakker, I. P. Lenaerts, M. Detheux, M. Parmentier, M. De, I, S. Scharpe, and J. Van Damme. 1999. CD26/dipeptidylpeptidase IV down-regulates the eosinophil chemotactic potency, but not the anti-HIV activity of human eotaxin by affecting its interaction with CC chemokine receptor 3. *J. Immunol.* 162:4903-4909.
47. Frohman, L. A., T. R. Downs, E. P. Heimer, and A. M. Felix. 1989. Dipeptidylpeptidase IV and trypsin-like enzymatic degradation of human growth hormone-releasing hormone in plasma. *J. Clin. Invest* 83:1533-1540.
48. Morimoto, C. and S. F. Schlossman. 1998. The structure and function of CD26 in the T-cell immune response. *Immunol. Rev.* 161:55-70.
49. Deacon, C. F., T. E. Hughes, and J. J. Holst. 1998. Dipeptidyl peptidase IV inhibition potentiates the insulinotropic effect of glucagon-like peptide 1 in the anesthetized pig. *Diabetes* 47:764-769.
50. Nauck, M. A., M. M. Heimesaat, C. Orskov, I. J. Holst, R. Ebert, and W. Creutzfeldt. 1993. Preserved incretin activity of glucagon-like peptide 1 [7-36 amide] but not of synthetic human gastric inhibitory polypeptide in patients with type-2 diabetes mellitus. *J. Clin. Invest* 91:301-307.
51. Moller, D. E. 2001. New drug targets for type 2 diabetes and the metabolic syndrome. *Nature* 414:821-827.
52. Proost, P., E. Schutyser, P. Menten, S. Struyf, A. Wuyts, G. Opdenakker, M. Detheux, M. Parmentier, C. Durinx, A. M. Lambeir, J. Neyts, S. Liekens, P. C. Maudgal, A. Billiau, and J. Van Damme. 2001. Amino-terminal truncation of CXCR3 agonists impairs receptor signaling and lymphocyte chemotaxis, while preserving antiangiogenic properties. *Blood* 98:3554-3561.
53. Loetscher, P., A. Pellegrino, J. H. Gong, I. Mattioli, M. Loetscher, G. Bardi, M. Baggiolini, and I. Clark-Lewis. 2001. The ligands of CXC chemokine receptor 3, I-TAC, Mig, and IP10, are natural antagonists for CCR3. *J Biol. Chem.* 276:2986-2991.
54. Proudfoot, A. E., C. A. Power, A. J. Hoogewerf, M. O. Montjovent, F. Borlat, R. E. Offord, and T. N. Wells. 1996. Extension of recombinant human RANTES by the retention of the initiating methionine produces a potent antagonist. *J. Biol. Chem.* 271:2599-2603.
55. Simmons, G., P. R. Clapham, L. Picard, R. E. Offord, M. M. Rosenkilde, T. W. Schwartz, R. Buser, T. N. C. Wells, and A. E. Proudfoot. 1997. Potent inhibition of HIV-1 infectivity in macrophages and lymphocytes by a novel CCR5 antagonist. *Science* 276:276-279.
56. Mosier, D. E., G. R. Picchio, R. J. Gulizia, R. Sabbe, P. Poignard, L. Picard, R. E. Offord, D. A. Thompson, and J. Wilken. 1999. Highly potent RANTES analogues either prevent CCR5-using human immunodeficiency virus type 1 infection in vivo or rapidly select for CXCR4-using variants. *J. Virol.* 73:3544-3550.
57. Simmons, G., J. D. Reeves, S. Hibbitts, J. T. Stine, P. W. Gray, A. E. Proudfoot, and P. R. Clapham. 2000. Co-receptor use by HIV and inhibition of HIV infection by chemokine receptor ligands. *Immunol. Rev.* 177:112-126.
58. Conn, P. M. and W. F. Crowley, Jr. 1994. Gonadotropin-releasing hormone and its analogs. *Annu. Rev. Med.* 45:391-405.
59. Ferguson, S. S. 2001. Evolving concepts in G protein-coupled receptor endocytosis: the role in receptor desensitization and signaling. *Pharmacol. Rev.* 53:1-24.
60. Loffet, A. 2002. Peptides as drugs: is there a market? *J. Pept. Sci.* 8:1-7.
61. Elsner, J., H. Petering, R. Hochstetter, D. Kimmig, T. N. Wells, A. Kapp, and A. E. Proudfoot. 1997. The CC chemokine antagonist Met-RANTES inhibits eosinophil effector functions through the chemokine receptors CCR1 and CCR3. *Eur. J. Immunol.* 27:2892-2898.
62. Ghirnikar, R. S., Y. L. Lee, and L. F. Eng. 2001. Chemokine antagonist infusion promotes axonal sparing after spinal cord contusion injury in rat. *J. Neurosci. Res.* 64:582-589.
63. Gong, J. H., M. Uguccioni, B. Dewald, M. Baggiolini, and I. Clark Lewis. 1996. RANTES and MCP-3 antagonists bind multiple chemokine receptors. *J. Biol. Chem.* 271: 10521-10527.

The invention claimed is:

1. A method of inhibiting the emigration of cells through a membrane limiting one body compartment from another comprising confronting the cells with an agonist specific for receptors involved with migration of the cells via a receptor thereby making the cells unresponsive to further activation for emigration, wherein the agonist is selected from a group consisting of n-nonanoyl-CCL14[10-74] and bis-n-nonanoyl-CCL14[10-74].

2. The method according to claim 1 wherein the emigration of cells is from the intravascular compartment into a tissue.

3. The method according to claim 2, wherein the cells are blood circulating cells and the intravascular compartment is the blood stream.

4. The method of claim 2 wherein the cells are leukocytes.

5. The method of claim 2 wherein confronting the cells is by administering a therapeutically effective amount of the agonist to a mammal for treating a disease state in the mammal alleviated by inhibiting the emigration of cells.

6. The method of claim 5 wherein the disease state is inflammation.

7. The method of claim 6 wherein the inflammation is effected by at least one of allergic asthma, atopic dermatitis, and rheumatoid arthritis.

* * * * *

SEQUENCE LISTING

```
<160> NUMBER OF SEQ ID NOS: 20

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: N-terminal
      sequence of CCL14 derivative CCL14[1-74]

<400> SEQUENCE: 1

Thr Lys Thr Glu Ser Ser Ser Arg Gly Pro Tyr His Pro Ser Glu Cys
 1               5                   10                  15

Cys
```

```
<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: N-terminal
      sequence of CCL14 derivative CCL14[6-74]

<400> SEQUENCE: 2

Ser Ser Arg Gly Pro Tyr His Pro Ser Glu Cys Cys
 1               5                  10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: N-terminal
      sequence of CCL14 derivative CCL14[7-74]

<400> SEQUENCE: 3

Ser Arg Gly Pro Tyr His Pro Ser Glu Cys Cys
 1               5                  10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: N-terminal
      sequence of CCL14 derivative CCL14[8-74]

<400> SEQUENCE: 4

Arg Gly Pro Tyr His Pro Ser Glu Cys Cys
 1               5                  10

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: N-terminal
      sequence of CCL14 derivative CCL14[9-74]

<400> SEQUENCE: 5

Gly Pro Tyr His Pro Ser Glu Cys Cys
 1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: N-terminal
      sequence of CCL11 (eotaxin)

<400> SEQUENCE: 6

Gly Pro Ala Ser Val Pro Thr Cys Cys
 1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: N-terminal
      sequence of CCL14 derivative  CCL14[10-74]
```

```
<400> SEQUENCE: 7

Pro Tyr His Pro Ser Glu Cys Cys
  1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: N-terminal
      sequence of CCL14 derivative CCL14[11-74]

<400> SEQUENCE: 8

Tyr His Pro Ser Glu Cys Cys
  1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: N-terminal
      sequence of CCL14 derivative CCL14[12-74]

<400> SEQUENCE: 9

His Pro Ser Glu Cys Cys
  1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: N-terminal
      sequence of CCL14 derivative CRIC3

<400> SEQUENCE: 10

Pro Tyr His Pro Ser Glu Cys Cys
  1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: N-terminal
      sequence of CCL14 derivative Bis-NNY-CCL14

<400> SEQUENCE: 11

Pro Tyr His Pro Ser Glu Cys Cys
  1               5

<210> SEQ ID NO 12
<211> LENGTH: 65
<212> TYPE: PRT
<213> ORGANISM: Artificial Sequence
<220> FEATURE:
<223> OTHER INFORMATION: Description of Artificial Sequence: N-terminal
      sequence of CCL14 derivative CCL14[10-74]

<400> SEQUENCE: 12

Pro Tyr His Pro Ser Glu Cys Cys Phe Thr Tyr Thr Thr Tyr Lys Ile
  1               5                  10                  15

Pro Arg Gln Arg Ile Met Asp Tyr Tyr Glu Thr Asn Ser Gln Cys Ser
                 20                  25                  30

Lys Pro Gly Ile Val Phe Ile Thr Lys Arg Gly His Ser Val Cys Thr
```

```
                 35                  40                  45

Asn Pro Ser Asp Lys Trp Val Gln Asp Tyr Ile Lys Asp Met Lys Glu
         50                  55                  60

Asn
 65

<210> SEQ ID NO 13
<211> LENGTH: 67
<212> TYPE: PRT
<213> ORGANISM: Artificial Sequence
<220> FEATURE:
<223> OTHER INFORMATION: Description of Artificial Sequence: N-terminal
      sequence of CXCL12 derivative CXCL12[1-67]

<400> SEQUENCE: 13

Lys Pro Val Ser Leu Ser Tyr Arg Cys Pro Cys Arg Phe Phe Glu Ser
 1               5                  10                  15

His Val Ala Arg Ala Asn Val Lys His Leu Lys Ile Leu Asn Thr Pro
             20                  25                  30

Asn Cys Ala Leu Gln Ile Val Ala Arg Leu Lys Asn Asn Asn Arg Gln
         35                  40                  45

Val Cys Ile Asp Pro Lys Leu Lys Trp Ile Gln Glu Tyr Leu Glu Lys
     50                  55                  60

Ala Leu Asn
 65

<210> SEQ ID NO 14
<211> LENGTH: 67
<212> TYPE: PRT
<213> ORGANISM: Artificial Sequence
<220> FEATURE:
<223> OTHER INFORMATION: Description of Artificial Sequence: N-terminal
      sequence of CXCL12 derivative CXCL12V3I[1-67]

<400> SEQUENCE: 14

Lys Pro Ile Ser Leu Ser Tyr Arg Cys Pro Cys Arg Phe Phe Glu Ser
 1               5                  10                  15

His Val Ala Arg Ala Asn Val Lys His Leu Lys Ile Leu Asn Thr Pro
             20                  25                  30

Asn Cys Ala Leu Gln Ile Val Ala Arg Leu Lys Asn Asn Asn Arg Gln
         35                  40                  45

Val Cys Ile Asp Pro Lys Leu Lys Trp Ile Gln Glu Tyr Leu Glu Lys
     50                  55                  60

Ala Leu Asn
 65

<210> SEQ ID NO 15
<211> LENGTH: 66
<212> TYPE: PRT
<213> ORGANISM: Artificial Sequence
<220> FEATURE:
<223> OTHER INFORMATION: Description of Artificial Sequence: N-terminal
      sequence of CXCL12 derivative CXCL12[2-67]

<400> SEQUENCE: 15

Pro Val Ser Leu Ser Tyr Arg Cys Pro Cys Arg Phe Phe Glu Ser His
 1               5                  10                  15

Val Ala Arg Ala Asn Val Lys His Leu Lys Ile Leu Asn Thr Pro Asn
             20                  25                  30

Cys Ala Leu Gln Ile Val Ala Arg Leu Lys Asn Asn Asn Arg Gln Val
         35                  40                  45
```

```
Cys Ile Asp Pro Lys Leu Lys Trp Ile Gln Glu Tyr Leu Glu Lys Ala
        50                  55                  60

Leu Asn
 65

<210> SEQ ID NO 16
<211> LENGTH: 66
<212> TYPE: PRT
<213> ORGANISM: Artificial Sequence
<220> FEATURE:
<223> OTHER INFORMATION: Description of Artificial Sequence: N-terminal
      sequence of CXCL12 derivative CXCL12V3I[2-67]

<400> SEQUENCE: 16

Pro Ile Ser Leu Ser Tyr Arg Cys Pro Cys Arg Phe Phe Glu Ser His
 1               5                  10                  15

Val Ala Arg Ala Asn Val Lys His Leu Lys Ile Leu Asn Thr Pro Asn
            20                  25                  30

Cys Ala Leu Gln Ile Val Ala Arg Leu Lys Asn Asn Asn Arg Gln Val
        35                  40                  45

Cys Ile Asp Pro Lys Leu Lys Trp Ile Gln Glu Tyr Leu Glu Lys Ala
        50                  55                  60

Leu Asn
 65

<210> SEQ ID NO 17
<211> LENGTH: 72
<212> TYPE: PRT
<213> ORGANISM: Artificial Sequence
<220> FEATURE:
<223> OTHER INFORMATION: Description of Artificial Sequence: N-terminal
      sequence of CXCL12 derivative CXCL12[1-72]

<400> SEQUENCE: 17

Lys Pro Val Ser Leu Ser Tyr Arg Cys Pro Cys Arg Phe Phe Glu Ser
 1               5                  10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
        50                  55                  60

Ala Leu Asn Lys Arg Phe Lys Met
 65                  70

<210> SEQ ID NO 18
<211> LENGTH: 72
<212> TYPE: PRT
<213> ORGANISM: Artificial Sequence
<220> FEATURE:
<223> OTHER INFORMATION: Description of Artificial Sequence: N-terminal
      sequence of CXCL12 derivative CXCL12V3I[1-72]

<400> SEQUENCE: 18

Lys Pro Ile Ser Leu Ser Tyr Arg Cys Pro Cys Arg Phe Phe Glu Ser
 1               5                  10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45
```

```
Val Cys Ile Asp Pro Lys Leu Lys Trp Ile Gln Glu Tyr Leu Glu Lys
            50                  55                  60

Ala Leu Asn Lys Arg Phe Lys Met
 65                  70

<210> SEQ ID NO 19
<211> LENGTH: 71
<212> TYPE: PRT
<213> ORGANISM: Artificial Sequence
<220> FEATURE:
<223> OTHER INFORMATION: Description of Artificial Sequence: N-terminal
      sequence of CXCL12 derivative CXCL12[2-72]

<400> SEQUENCE: 19

Pro Val Ser Leu Ser Tyr Arg Cys Pro Cys Arg Phe Phe Glu Ser His
  1               5                  10                  15

Val Ala Arg Ala Asn Val Lys His Leu Lys Ile Leu Asn Thr Pro Asn
                 20                  25                  30

Cys Ala Leu Gln Ile Val Ala Arg Leu Lys Asn Asn Asn Arg Gln Val
             35                  40                  45

Cys Ile Asp Pro Lys Leu Lys Trp Ile Gln Glu Tyr Leu Glu Lys Ala
         50                  55                  60

Leu Asn Lys Arg Phe Lys Met
 65                  70

<210> SEQ ID NO 20
<211> LENGTH: 71
<212> TYPE: PRT
<213> ORGANISM: Artificial Sequence
<220> FEATURE:
<223> OTHER INFORMATION: Description of Artificial Sequence: N-terminal
      sequence of CXCL12 derivative CXCL12V3I[2-72]

<400> SEQUENCE: 20

Pro Ile Ser Leu Ser Tyr Arg Cys Pro Cys Arg Phe Phe Glu Ser His
  1               5                  10                  15

Val Ala Arg Ala Asn Val Lys His Leu Lys Ile Leu Asn Thr Pro Asn
                 20                  25                  30

Cys Ala Leu Gln Ile Val Ala Arg Leu Lys Asn Asn Asn Arg Gln Val
             35                  40                  45

Cys Ile Asp Pro Lys Leu Lys Trp Ile Gln Glu Tyr Leu Glu Lys Ala
         50                  55                  60

Leu Asn Lys Arg Phe Lys Met
 65                  70
```